United States Patent
Ryu et al.

(10) Patent No.: US 10,134,582 B2
(45) Date of Patent: Nov. 20, 2018

(54) TANTALUM COMPOUND AND METHODS OF FORMING THIN FILM AND FABRICATING INTEGRATED CIRCUIT DEVICE BY USING THE SAME

(71) Applicant: SAMSUNG ELECTRONICS CO., LTD., Suwon-si, Gyeonggi-do (KR)

(72) Inventors: Seung-min Ryu, Hwaseong-si (KR); Takanori Koide, Tokyo (JP); Naoki Yamada, Tokyo (JP); Jae-soon Lim, Seoul (KR); Tsubasa Shiratori, Tokyo (JP); Youn-joung Cho, Hwaseong-si (KR)

(73) Assignees: SAMSUNG ELECTRONICS CO., LTD., Suwon-si, Gyeonggi-do (KR); ADEKA CORPORATION, Tokyo (JP)

( * ) Notice: Subject to any disclaimer, the term of this patent is extended or adjusted under 35 U.S.C. 154(b) by 0 days.

(21) Appl. No.: 15/298,275

(22) Filed: Oct. 20, 2016

(65) Prior Publication Data
US 2017/0178961 A1    Jun. 22, 2017

(30) Foreign Application Priority Data

Dec. 21, 2015    (KR) .................. 10-2015-0182788

(51) Int. Cl.
  *H01L 21/44*    (2006.01)
  *H01L 23/52*    (2006.01)
  (Continued)

(52) U.S. Cl.
  CPC ........ *H01L 21/02183* (2013.01); *C07F 9/00* (2013.01); *C23C 16/16* (2013.01);
  (Continued)

(58) Field of Classification Search
  CPC .................................................. H01L 21/02183
  (Continued)

(56) References Cited

U.S. PATENT DOCUMENTS 6,015,917 A   1/2000  Bhandari et al.
6,139,922 A   10/2000 Kaloyeros et al.
(Continued)

FOREIGN PATENT DOCUMENTS

CN    1675407 A     5/2005
JP    2004-250431 A  9/2004
(Continued)

OTHER PUBLICATIONS

2017:1037364 HCAPLUS "Tantalum compound and methods of forming thin films . . ." by Seung-Min Ryu, Takanori Koide, Naoki Yamada, Jae-Soon Lim, Tsubasa Shiratori, Youn-Joung Cho (Assignee: Adeka Corporation).*
(Continued)

*Primary Examiner* — Calvin Lee
(74) *Attorney, Agent, or Firm* — Lee & Morse, P.C.

(57) ABSTRACT

A tantalum compound, a method of forming a thin film, and a method of fabricating an integrated circuit device, the tantalum compound being represented by the following General Formula (I):

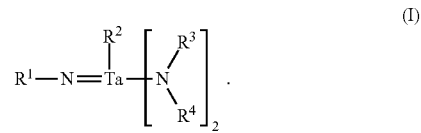

10 Claims, 34 Drawing Sheets

(51) Int. Cl.
*H01L 21/02* (2006.01)
*C07F 9/00* (2006.01)
*C23C 16/16* (2006.01)
*C23C 16/34* (2006.01)
*C23C 16/40* (2006.01)
*C23C 16/44* (2006.01)
*C23C 16/455* (2006.01)

(52) U.S. Cl.
CPC ............ *C23C 16/34* (2013.01); *C23C 16/405* (2013.01); *C23C 16/4401* (2013.01); *C23C 16/4412* (2013.01); *C23C 16/45525* (2013.01); *H01L 21/0215* (2013.01); *H01L 21/0228* (2013.01)

(58) Field of Classification Search
USPC ......... 257/757, 761, 768; 438/648, 656, 685
See application file for complete search history.

(56) References Cited

U.S. PATENT DOCUMENTS

| | | | |
|---|---|---|---|
| 6,379,748 B1 | 4/2002 | Bhandari et al. | |
| 6,485,784 B1 | 11/2002 | Leedham et al. | |
| 6,773,476 B2 * | 8/2004 | Sakai | C09G 1/02 51/307 |
| 7,098,131 B2 * | 8/2006 | Kang | C23C 16/34 438/648 |
| 7,148,367 B2 | 12/2006 | Itsuki | |
| 7,208,427 B2 | 4/2007 | Roeder et al. | |
| 7,407,881 B2 * | 8/2008 | Lee | H01L 21/28562 257/E21.171 |
| 7,459,392 B2 * | 12/2008 | Johnston | H01L 21/76843 438/650 |
| 7,592,471 B2 * | 9/2009 | Sekimoto | H01L 21/4763 556/43 |
| 7,736,697 B2 | 6/2010 | Thompson et al. | |
| 7,858,816 B2 * | 12/2010 | Chen | C23C 16/18 257/751 |
| 9,085,823 B2 | 7/2015 | Blasco et al. | |
| 2007/0054046 A1 | 3/2007 | Ishizaka et al. | |

FOREIGN PATENT DOCUMENTS

| | | |
|---|---|---|
| JP | 2007-246513 A | 9/2007 |
| JP | 2011-530002 A | 12/2011 |
| KR | 10-2008-0075561 A | 8/2008 |
| KR | 10-2012-0058762 A | 6/2012 |
| KR | 10-2013-0049020 A | 5/2013 |

OTHER PUBLICATIONS

Chinese Office action dated Sep. 13, 2018 for related application CN 201610994787.7.

\* cited by examiner

TANTALUM COMPOUND AND METHODS OF FORMING THIN FILM AND FABRICATING INTEGRATED CIRCUIT DEVICE BY USING THE SAME

CROSS-REFERENCE TO RELATED APPLICATION

Korean Patent Application No. 10-2015-0182788, filed on Dec. 21, 2015, in the Korean Intellectual Property Office, and entitled: "Tantalum Compound and Methods of Forming Thin Film and Fabricating Integrated Circuit Device by Using the Same," is incorporated by reference herein in its entirety.

BACKGROUND

1. Field

Embodiments relate to a tantalum compound and methods of forming a thin film and fabricating an integrated circuit device by using the same.

2. Description of the Related Art

Due to the development of electronic technologies, downscaling of semiconductor devices has been quickly carried out in recent years. Thus, patterns constituting electronic devices are becoming finer.

SUMMARY

Embodiments are directed to a tantalum compound and methods of forming a thin film and fabricating an integrated circuit device by using the same.

The embodiments may be realized by providing a tantalum compound represented by the following General Formula (I):

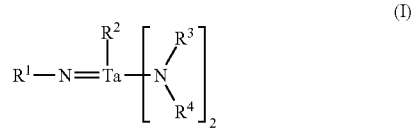

wherein, in General Formula I, $R^1$, $R^3$, and $R^4$ are each independently a C1 to C10 substituted or unsubstituted linear or branched alkyl, alkenyl, or alkynyl group, or a C4 to C20 substituted or unsubstituted aromatic or alicyclic hydrocarbon group; and $R^2$ is a hydrogen atom, a C1 to C10 substituted or unsubstituted linear or branched alkyl, alkenyl, or alkynyl group, or a C6 to C20 substituted or unsubstituted aromatic or alicyclic hydrocarbon group.

The embodiments may be realized by providing a method of forming a thin film, the method including forming a tantalum-containing film on a substrate by using a tantalum compound represented by the following General Formula (I):

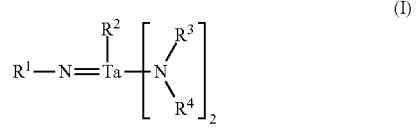

wherein, in General Formula (I), $R^1$, $R^3$, and $R^4$ are each independently a C1 to C10 substituted or unsubstituted linear or branched alkyl, alkenyl, or alkynyl group, or a C4 to C20 substituted or unsubstituted aromatic or alicyclic hydrocarbon group; and $R^2$ is a hydrogen atom, a C1 to C10 substituted or unsubstituted linear or branched alkyl, alkenyl, or alkynyl group, or a C6 to C20 substituted or unsubstituted aromatic or alicyclic hydrocarbon group.

The embodiments may be realized by providing a method of fabricating an integrated circuit device, the method including forming a lower structure on a substrate; and forming a tantalum-containing film on the lower structure by using a tantalum compound represented by the following General Formula (I):

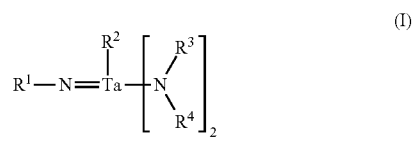

wherein, in General Formula I, $R^1$, $R^3$, and $R^4$ are each independently a C1 to C10 substituted or unsubstituted linear or branched alkyl, alkenyl, or alkynyl group, or a C4 to C20 substituted or unsubstituted aromatic or alicyclic hydrocarbon group; and $R^2$ is a hydrogen atom, a C1 to C10 substituted or unsubstituted linear or branched alkyl, alkenyl, or alkynyl group, or a C6 to C20 substituted or unsubstituted aromatic or alicyclic hydrocarbon group.

BRIEF DESCRIPTION OF THE DRAWINGS

Features will be apparent to those of skill in the art by describing in detail exemplary embodiments with reference to the attached drawings in which:

FIG. 4A illustrates perspective views of main components of the integrated circuit device which includes first and second transistors having FinFET structures, FIG. 4B illustrates cross-sectional views taken along lines B1-B1' and B2-B2' of FIG. 4A, and FIG. 4C illustrates cross-sectional views taken along lines C1-C1' and C2-C2' of FIG. 4A;

DETAILED DESCRIPTION

Figure 1:
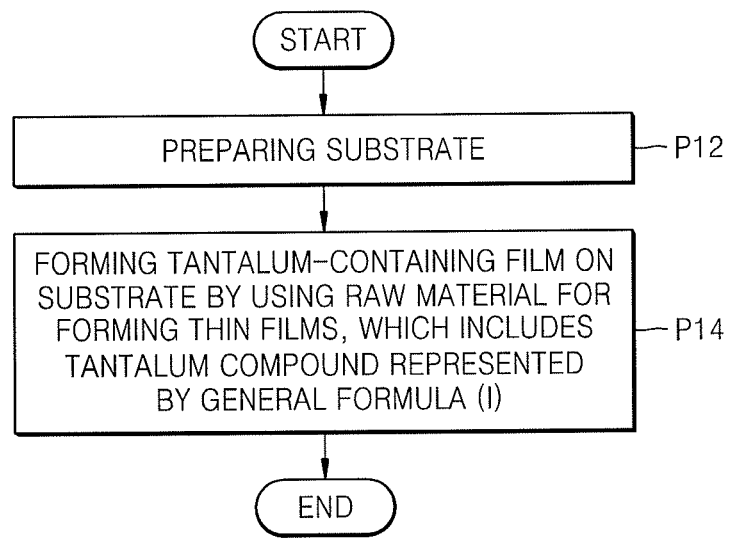
FIG. 1 illustrates a flowchart of a method of forming a thin film, according to embodiments.

According to an embodiment, a tantalum compound may be represented by the following General Formula (I).

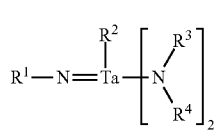

(I)

In General Formula (I), $R^1$, $R^3$, and $R^4$ may each independently be or include, e.g., a C1 to C10 substituted or unsubstituted linear or branched alkyl, alkenyl, or alkynyl group, or a C4 to C20 substituted or unsubstituted aromatic or alicyclic hydrocarbon group. $R^2$ may be or may include, e.g., a hydrogen atom, a C1 to C10 substituted or unsubstituted linear or branched alkyl, alkenyl, or alkynyl group, or a C6 to C20 substituted or unsubstituted aromatic or alicyclic hydrocarbon group.

In an implementation, $R^1$, $R^3$, and $R^4$ may each independently be, e.g., a C1 to C10 linear or branched alkyl group. In an implementation, $R^1$, $R^3$, and $R^4$ may each independently be, e.g., a C1 to C5 linear or branched alkyl group or a C1 to C4 linear or branched alkyl group.

In an implementation, $R^2$ may be, e.g., a C1 to C10 linear or branched alkyl group. In an implementation, $R^2$ may be, e.g., a C1 to C5 linear or branched alkyl group or a C1 to C3 linear or branched alkyl group.

In an implementation, the tantalum compound represented by General Formula (I) may be a liquid at room temperature or under ambient conditions. For example, the tantalum compound represented by General Formula (I) may be a liquid at 25° C. and 1 atmosphere (atm).

In an implementation, $R^1$, $R^2$, $R^3$, and $R^4$ may each independently be, e.g., a linear or branched alkyl group such as a methyl, ethyl, propyl, isopropyl, butyl, isobutyl, secondary butyl, tertiary butyl, pentyl, isoamyl, secondary amyl, or tertiary amyl group. In an implementation, at least one of $R^1$, $R^2$, $R^3$, and $R^4$ may be, e.g., an alicyclic alkyl group such as a cyclopentyl group.

When $R^1$ is a branched secondary alkyl group, the tantalum compound may exhibit improved stability and increased vapor pressure. Examples of the branched secondary alkyl group may include isopropyl, secondary butyl, and secondary amyl groups. In an implementation, to increase the vapor pressure of the tantalum compound, $R^1$ may be an isopropyl or secondary butyl group.

When $R^2$ is a linear primary alkyl group, the tantalum compound may exhibit improved stability and increased vapor pressure. Examples of the linear primary alkyl group may include methyl, ethyl, propyl, butyl, and amyl groups. In an implementation, to increase the vapor pressure of the tantalum compound, $R^2$ may be a methyl or ethyl group. When $R^2$ is a methyl group, the tantalum compound may facilitate formation of a tantalum-containing film including an extremely low amount of carbon residues through a process of forming a tantalum-containing thin film using an atomic layer deposition (ALD) process.

When $R^3$ is a branched secondary alkyl group, the tantalum compound may exhibit improved stability and increased vapor pressure. Examples of the branched secondary alkyl group may include isopropyl, secondary butyl, and secondary amyl groups. In an implementation, to increase the vapor pressure of the tantalum compound, $R^3$ may be an isopropyl or secondary butyl group.

In an implementation, the tantalum compound may include a tantalum compound represented by one of the following Formulae 1 to 54.

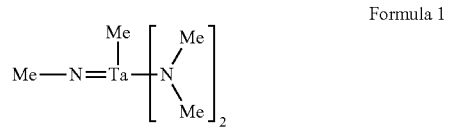

Formula 1

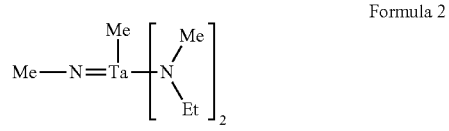

Formula 2

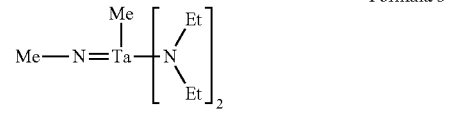

Formula 3

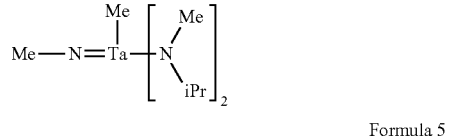

Formula 4

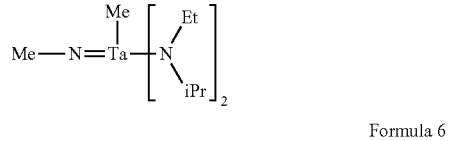

Formula 5

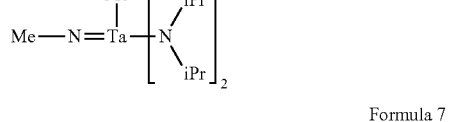

Formula 6

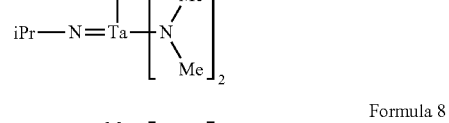

Formula 7

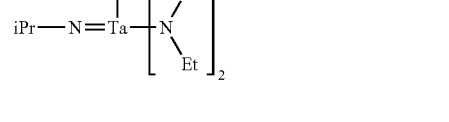

Formula 8

Formula 9
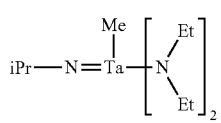
Formula 10
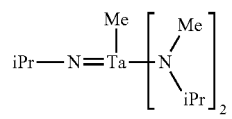
Formula 11
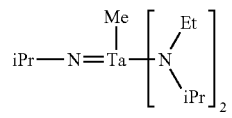
Formula 12
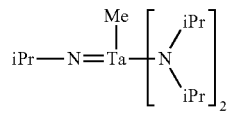
Formula 13
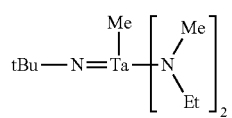
Formula 14
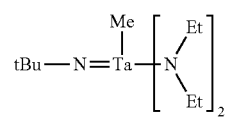
Formula 15
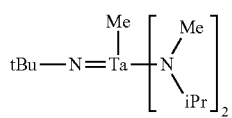
Formula 16
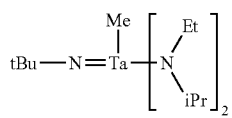
Formula 17
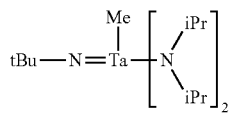
Formula 18
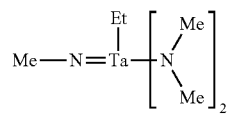
Formula 19
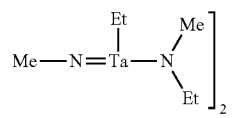
Formula 20
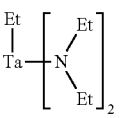
Formula 21
Formula 22
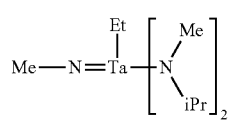
Formula 23
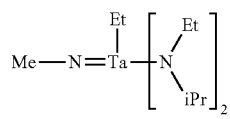
Formula 24
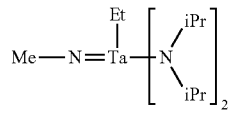
Formula 25
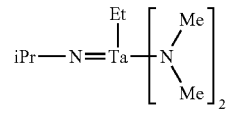
Formula 26
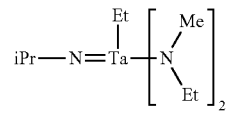
Formula 27
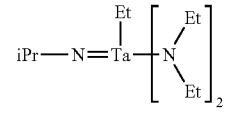
Formula 28
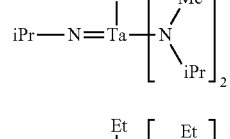
Formula 29
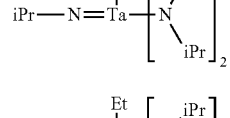
Formula 30
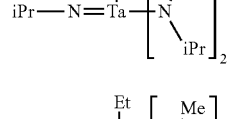
Formula 31
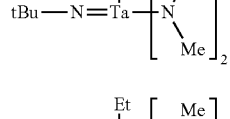
Formula 32
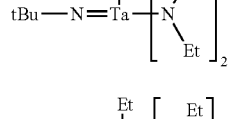
Formula 33
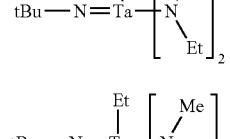
Formula 34

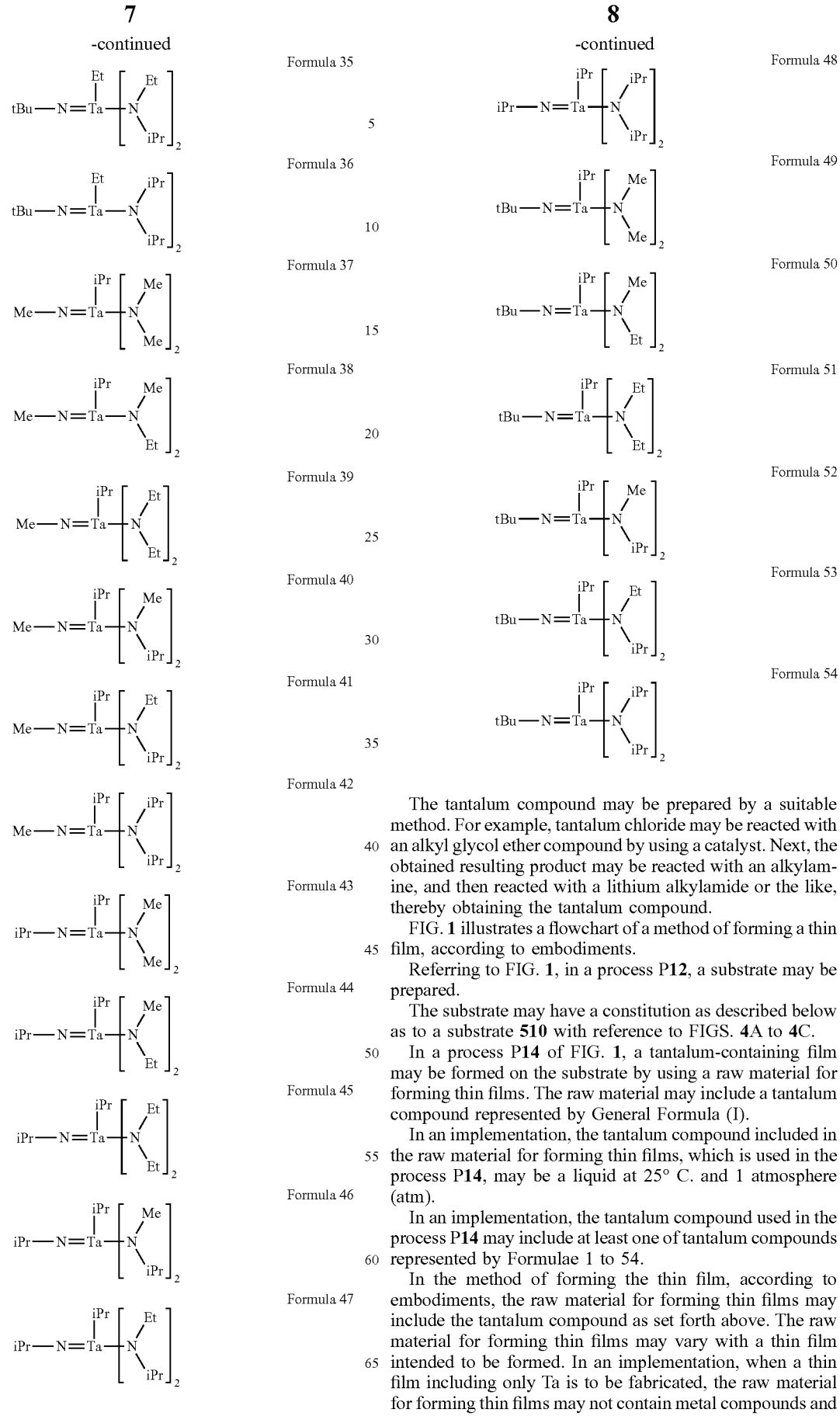

The tantalum compound may be prepared by a suitable method. For example, tantalum chloride may be reacted with an alkyl glycol ether compound by using a catalyst. Next, the obtained resulting product may be reacted with an alkylamine, and then reacted with a lithium alkylamide or the like, thereby obtaining the tantalum compound.

FIG. 1 illustrates a flowchart of a method of forming a thin film, according to embodiments.

Referring to FIG. 1, in a process P12, a substrate may be prepared.

The substrate may have a constitution as described below as to a substrate 510 with reference to FIGS. 4A to 4C.

In a process P14 of FIG. 1, a tantalum-containing film may be formed on the substrate by using a raw material for forming thin films. The raw material may include a tantalum compound represented by General Formula (I).

In an implementation, the tantalum compound included in the raw material for forming thin films, which is used in the process P14, may be a liquid at 25° C. and 1 atmosphere (atm).

In an implementation, the tantalum compound used in the process P14 may include at least one of tantalum compounds represented by Formulae 1 to 54.

In the method of forming the thin film, according to embodiments, the raw material for forming thin films may include the tantalum compound as set forth above. The raw material for forming thin films may vary with a thin film intended to be formed. In an implementation, when a thin film including only Ta is to be fabricated, the raw material for forming thin films may not contain metal compounds and semimetal compounds other than the tantalum compound. In an implementation, when a thin film including two or more metals and/or semimetals is to be fabricated, the raw material for forming thin films may include a compound (referred to as the term "another precursor" hereinafter) including a desired metal or semimetal, in addition to the tantalum compound. In an implementation, the raw material for forming thin films may include an organic solvent or a nucleophilic reagent in addition to the tantalum compound.

The raw material for forming thin films, which includes the tantalum compound, may be suitably used for chemical vapor deposition (CVD) and ALD processes in terms of properties thereof.

When the raw material for forming thin films is a raw material for use in a CVD process, the composition of the raw material for forming thin films may be selected according to a specific method of the CVD process, a raw material transfer method, or the like.

The raw material transfer method may include a gas transfer method and a liquid transfer method. In the gas transfer method, a raw material for CVD is made to be in a vapor state by vaporizing the raw material through heating and/or reduced pressure in a container (which may be referred to as the term "raw material container" hereinafter) in which the raw material is stored, and the vapor-state raw material and a carrier gas (e.g., argon, nitrogen, helium, or the like, which is used as needed), may be introduced together into a chamber (which may be referred to as the term "deposition reactor" hereinafter) in which the substrate is placed. In the liquid transfer method, a raw material for CVD may be transferred in a liquid or solution state to a vaporizer, and made into vapor by vaporizing the raw material through heating and/or reduced pressure in the vaporizer, followed by introducing the vapor into a chamber. In the gas transfer method, the tantalum compound itself represented by General Formula (I) may be used as a CVD raw material. In an implementation, the CVD raw material may further include another precursor, a nucleophilic reagent, or the like.

In an implementation, in the method of forming the thin film, to form the tantalum-containing film, a multi-component CVD process may be used. In the multi-component CVD process, a method of supplying raw material compounds, which will be used for the CVD process, independently for each component (hereinafter, the method may be referred to as the term "single source method"), or a method of supplying a multi-component raw material by vaporizing a raw material mixture in which the multi-component raw material is mixed to desired composition (hereinafter, the method may be referred to as the term "multi-component source method") may be used. When the multi-component source method is used, a first mixture including the tantalum compound, a first mixed solution in which the first mixture is dissolved in an organic solvent, a second mixture including the tantalum compound and another precursor, or a second mixed solution in which the second mixture is dissolved in an organic solvent, may be used as a raw material compound for forming thin films in the CVD process. Each of the first and second mixtures and the first and second mixed solutions may further include a nucleophilic reagent.

In an implementation, the organic solvent may include, e.g., acetate esters such as ethyl acetate and methoxyethyl acetate; ethers such as tetrahydrofuran, tetrahydropyran, ethylene glycol dimethyl ether, diethylene glycol dimethyl ether, triethylene glycol dimethyl ether, dibutyl ether, and dioxane; ketones such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons such as hexane, cyclohexane, methylcyclohexane, dimethylcyclohexane, ethylcyclohexane, heptane, octane, toluene, and xylene; cyano group-containing hydrocarbons such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; pyridine; lutidine, or the like. The organic solvents set forth above as examples may be used alone or in combination, by taking into account solubility of a solute, temperatures for use thereof and melting points thereof, flash points thereof, or the like. In an implementation, a total concentration of the tantalum compound and another precursor may be about 0.01 mol/L to about 2.0 mol/L, e.g., about 0.05 mol/L to about 1.0 mol/L, in the organic solvent. Here, the total concentration of the tantalum compound and the other precursor refers to a concentration of the tantalum compound when the raw material for forming thin films does not include metal compounds and semimetal compounds other than the tantalum compound, and refers to the sum of amounts of the tantalum compound and the other precursor when the raw material for forming thin films further includes, in addition to the tantalum compound, a compound containing other metals than tantalum or a compound containing semimetals.

In the method of forming the thin film, when the multi-component CVD process is used to form the tantalum-containing film, the other precursor capable of being used together with the tantalum compound may include a suitable precursor that is capable of being used as raw materials in a CVD process.

In an implementation, the other precursor (capable of being used in the method of forming the thin film) may include a Si or metal compound, e.g., a compound having hydride, hydroxide, halide, azide, alkyl, alkenyl, cycloalkyl, allyl, alkynyl, amino, dialkylaminoalkyl, monoalkylamino, dialkylamino, diamino, di(silyl-alkyl)amino, di(alkyl-silyl)amino, disilylamino, alkoxy, alkoxyalkyl, hydrazide, phosphide, nitrile, dialkylaminoalkoxy, alkoxyalkyldialkylamino, siloxy, diketonate, cyclopentadienyl, silyl, pyrazolate, guanidinate, phosphoguanidinate, amidinate, ketoiminate, diketoiminate, carbonyl, and phosphoamidinate groups as ligands.

In an implementation, a metal included in the precursor may include, e.g., magnesium (Mg), calcium (Ca), strontium (Sr), barium (Ba), radium (Ra), scandium (Sc), yttrium (Y), titanium (Ti), zirconium (Zr), hafnium (Hf), vanadium (V), niobium (Nb), chromium (Cr), molybdenum (Mo), tungsten (W), manganese (Mn), iron (Fe), osmium (Os), cobalt (Co), rhodium (Rh), iridium (Ir), nickel (Ni), palladium (Pd), platinum (Pt), copper (Cu), silver (Ag), gold (Au), zinc (Zn), cadmium (Cd), aluminum (Al), gallium (Ga), indium (In), germanium (Ge), tin (Sn), lead (Pb), antimony (Sb), bismuth (Bi), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), or the like.

In an implementation, when an alcohol compound is used as an organic ligand, the precursor may be prepared by reacting an inorganic salt of the metal set forth above or a hydrate thereof with an alkali metal alkoxide of the alcohol compound. In an implementation, examples of the inorganic salt of the metal or the hydrate thereof may include a halide, a nitrate, and the like of the metal, and examples of the alkali metal alkoxide may include sodium alkoxide, lithium alkoxide, potassium alkoxide, and the like.

In the single source method, as the other precursor, a compound exhibiting thermal and/or oxidative decomposition behaviors that are similar to those of the tantalum compound may be used. In addition, in the multi-component source method, it is suitable to use a compound that exhibits thermal and/or oxidative decomposition behaviors similar to those of the tantalum compound and is not altered by chemical reactions or the like upon mixing thereof, as the other precursor.

Among the examples of the other precursor, examples of a Ti, Zr, or Hf-containing precursor may include compounds represented by Formulae (II-1) to (II-5):

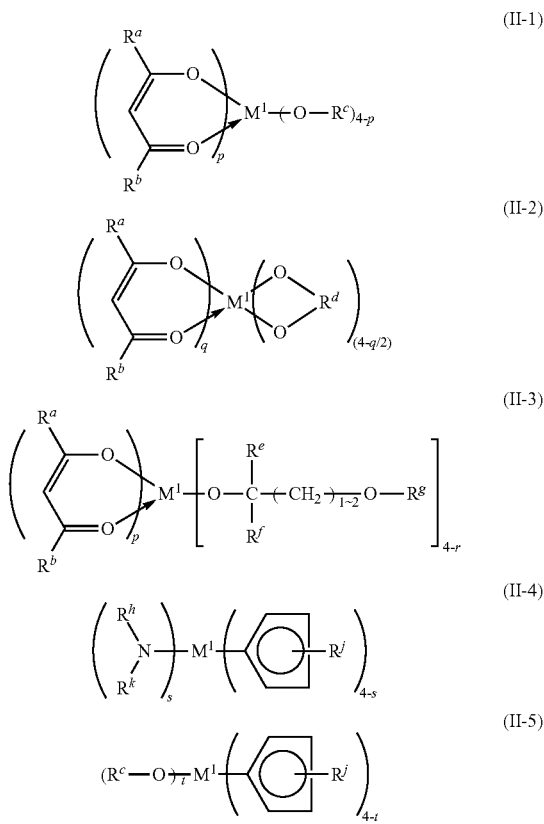

In the above Formulae (II-1) to (II-5), $M^1$ may be, e.g., Ti, Zr, or Hf.

$R^a$ and $R^b$ may each independently be or include, e.g., a C1 to C20 alkyl group which may be substituted with a halogen atom and may include an oxygen atom in a chain.

$R^c$ may be or include, e.g., a C1 to C8 alkyl group. $R^d$ may be or include, e.g., a C2 to C18 linear or branched alkylene group. $R^e$ and $R^f$ may each independently be, e.g., a hydrogen atom or a C1 to C3 alkyl group. $R^g$, $R^h$, $R^j$, and $R^k$ may each independently be, e.g., a hydrogen atom or a C1 to C4 alkyl group. p may be, e.g., an integer of 0 to 4. q may be, e.g., 0 or 2. r may be, e.g., an integer of 0 to 3. s may be, e.g., an integer of 0 to 4. t may be, e.g., an integer of 1 to 4.

In an implementation, in Formulae (II-1) to (II-5), $R^a$ and $R^b$ may each independently be or include, e.g., a methyl, ethyl, propyl, isopropyl, butyl, sec-butyl, tert-butyl, isobutyl, amyl, isoamyl, sec-amyl, tert-amyl, hexyl, heptyl, 3-heptyl, isoheptyl, tert-heptyl, n-octyl, isooctyl, tert-octyl, 2-ethylhexyl, trifluoromethyl, perfluorohexyl, 2-methoxyethyl, 2-ethoxyethyl, 2-butoxyethyl, 2-(2-methoxyethoxy)ethyl, 1-methoxy-1,1-dimethylmethyl, 2-methoxy-1,1-dimethylethyl, 2-ethoxy-1,1-dimethylethyl, 2-isopropoxy-1,1-dimethylethyl, 2-butoxy-1,1-dimethylethyl, or 2-(2-methoxyethoxy)-1,1-dimethylethyl group.

In an implementation, in Formulae (II-1) to (II-5), $R^c$ may be or include, e.g., a methyl, ethyl, propyl, isopropyl, butyl, sec-butyl, tert-butyl, isobutyl, amyl, isoamyl, sec-amyl, tert-amyl, hexyl, 1-ethylpentyl, heptyl, isoheptyl, tert-heptyl, n-octyl, isooctyl, tert-octyl, or 2-ethylhexyl group.

In an implementation, in Formulae (II-1) to (II-5), $R^d$ may be, e.g., a group obtained by or from a glycol. In an implementation, $R^d$ may be or include, e.g., a group obtained from a 1,2-ethanediol, 1,2-propanediol, 1,3-butanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, or 1-methyl-2,4-pentanediole.

In an implementation, in Formulae (II-1) to (II-5), $R^e$ and $R^f$ may each independently be or include, e.g., a methyl, ethyl, propyl, or 2-propyl group.

In an implementation, in Formulae (II-1) to (II-5), $R^g$, $R^h$, $R^j$, and $R^k$ may each independently be or include, e.g., a methyl, ethyl, propyl, isopropyl, butyl, sec-butyl, tert-butyl, or isobutyl group.

In an implementation the Ti-containing precursor may include, e.g., tetrakis alkoxy titanium compounds such as tetrakis(ethoxy) titanium, tetrakis(2-propoxy) titanium, tetrakis(butoxy) titanium, tetrakis(sec-butoxy) titanium, tetrakis(isobutoxy) titanium, tetrakis(3-butoxy) titanium, tetrakis(tert-pentoxy) titanium, and tetrakis(1-methoxy-2-methyl-2-propoxy) titanium; tetrakis β-diketonato titanium compounds such as tetrakis(pentane-2,4-dionato) titanium, tetrakis(2,6-dimethylheptane-3,5-dionato) titanium, and tetrakis(2,2,6,6-tetramethylheptane-3,5-dionato) titanium; bis(alkoxy) bis(β-diketonato) titanium compounds such as bis(methoxy) bis(pentane-2,4-dionato) titanium, bis(ethoxy) bis(pentane-2,4-dionato) titanium, bis(tert-butoxy) bis(pentane-2,4-dionato) titanium, bis(methoxy) bis(2,6-dimethylheptane-3,5-dionato) titanium, bis(ethoxy) bis(2,6-dimethylheptane-3,5-dionato) titanium, bis(2-propoxy) bis(2,6-dimethylheptane-3,5-dionato) titanium, bis(tert-butoxy) bis(2,6-dimethylheptane-3,5-dionato) titanium, bis(tert-amyloxy) bis(2,6-dimethylheptane-3,5-dionato) titanium, bis(methoxy) bis(2,2,6,6-tetramethylheptane-3,5-dionato) titanium, bis(ethoxy) bis(2,2,6,6-tetramethylheptane-3,5-dionato) titanium, bis(2-propoxy) bis(2,2,6,6-tetramethylheptane-3,5-dionato) titanium, bis(3-butoxy) bis(2,2,6,6-tetramethylheptane-3,5-dionato) titanium, and bis(tert-amyloxy) bis(2,2,6,6-tetramethylheptane-3,5-dionato) titanium; glycoxy bis(β-diketonato) titaniums such as (2-methylpentanedihydroxy) bis(2,2,6,6-tetramethylheptane-3,5-dionato) titanium and (2-methylpentanedihydroxy) bis(2,6-dimethylheptane-3,5-dionato) titanium; (cyclopentadienyl) tris(dialkylamino) titaniums such as (methylcyclopentadienyl) tris(dimethylamino) titanium, (ethylcyclopentadienyl) tris(dimethylamino) titanium, (cyclopentadienyl) tris(dimethylamino) titanium, (methylcyclopentadienyl) tris(ethylmethylamino) titanium, (ethylcyclopentadienyl) tris(ethylmethylamino) titanium, (cyclopentadienyl) tris(ethylmethylamino) titanium, (methylcyclopentadienyl) tris(diethylamino) titanium, (ethylcyclopentadienyl) tris(diethylamino) titanium, and (cyclopentadienyl) tris(diethylamino) titanium; (cyclopentadienyl) tris(alkoxy) titaniums such as (cyclopentadienyl) tris(methoxy) titanium, (methylcyclopentadienyl) tris(methoxy) titanium, (ethylcyclopentadienyl) tris(methoxy) titanium, (propylcyclopentadienyl) tris(methoxy) titanium, (isopropylcyclopentadienyl) tris(methoxy) titanium, (butylcyclopentadienyl) tris(methoxy) titanium, (isobutylcyclopentadienyl) tris(methoxy) titanium, (tert-butylcyclopentadienyl) tris(methoxy) titanium, and (pentamethylcyclopentadienyl) tris(methoxy) titanium, and the like.

Examples of the Zr-containing precursor and the Hf-containing precursor may include compounds obtained by substituting titanium of the compounds set forth above as examples of the Ti-containing precursor with zirconium or hafnium.

Examples of a rare-earth element-containing precursor may include compounds represented by Formulae (III-1) to (III-3).

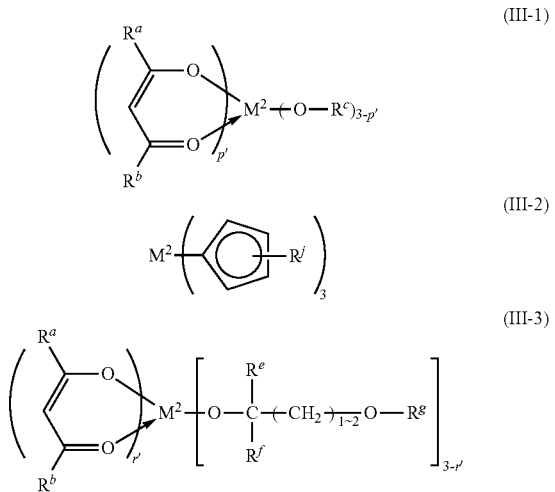

In Formulae (III-1) to (III-3), $M^2$ may be, e.g., a rare-earth element. $R^a$ and $R^b$ may each independently be or include, e.g., a C1 to C20 alkyl group, which may be substituted at a halogen atom and may include an oxygen atom in a ring. $R^c$ may be or may include, e.g., a C1 to C8 alkyl group. $R^e$ and $R^f$ may each independently be or include, e.g., a hydrogen atom or a C1 to C3 alkyl group. $R^g$ and $R^j$ may each independently be or include, e.g., a C1 to C4 alkyl group. p' may be, e.g., an integer of 0 to 3. r' may be, e.g., an integer of 0 to 2.

In the rare-earth element-containing precursors represented by Formulae (III-1) to (III-3), the rare-earth element denoted by $M^2$ may be, e.g., scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), or ytterbium (Yb). In Formulae (III-1) to (III-3), each of $R^a$, $R^b$, $R^c$, $R^e$, $R^f$, $R^g$, and $R^j$ may be the same as described with reference to Formulae (II-1) to (II-5).

In the method of forming the thin film, the raw material for forming thin films may include a nucleophilic reagent in order to impart stability to the tantalum compound and the other precursor. In an implementation, examples of the nucleophilic reagent capable of being included in the raw material for forming thin films may include ethylene glycol ethers such as glyme, diglyme, triglyme, and tetraglyme; crown ethers such as 18-crown-6, dicyclohexyl-18-crown-6, 24-crown-8, dicyclohexyl-24-crown-8, and dibenzo-24-crown-8; polyamines such as ethylenediamine, N,N,N',N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethylenetetramine; cyclic polyamines such as cyclam and cyclen; heterocyclic compounds such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters such as methyl acetoacetate, ethyl acetoacetate, and 2-methoxyethyl acetoacetate; and β-diketones such as acetylacetone, 2,4-hexanedione, 2,4-heptanedione, 3,5-heptanedione, and dipivaloyl methane.

In an implementation, the nucleophilic reagent may be present in an amount of about 0.1 mol to about 10 mol, e.g., about 1 mol to about 4 mol, based on 1 mol of the total amount of the precursor.

In the raw material for forming thin films, which is used in the method of forming the thin film, suppressing amounts of impurities of metal elements, halogens such as chlorine, organic materials, and the like as much as possible may be desirable. In an implementation, each of the metal element impurities may be present in an amount of about 100 ppb or less in the raw material for forming thin films. In an implementation, the raw material for forming thin films may include about 10 ppb or less of each of the metal element impurities, and the total amount of the metal impurities may be about 1 ppm or less, e.g., about 100 ppb or less. In an implementation, when a thin film, which is used as a gate insulating film, gate conductive film, or barrier film of a large-scale integrated (LSI) circuit, is formed, amounts of alkali metal and alkali earth metal elements, which affect electrical properties of an obtained thin film, may be reduced as much as possible. In an implementation, the halogen impurities may be present in an amount of about 100 ppm or less, e.g., about 10 ppm or less, in the raw material for forming thin films.

In an implementation, the organic component impurities may be present in the total amount of about 500 ppm or less, e.g., about 50 ppm or less or about 10 ppm or less, in the raw material for forming thin films.

If moisture is present in the raw material for forming thin films, the moisture may cause generation of particles in the raw material for CVD, or generation of particles during formation of the thin film. Therefore, moisture may be removed in advance from the metal compound, the organic solvent, and the nucleophilic reagent before use thereof. Moisture may be present in an amount of about 10 ppm or less, e.g., about 1 ppm or less, in each of the metal compound, the organic solvent, and the nucleophilic reagent.

To reduce particle contamination in the thin film intended to be formed, an amount of particles in the raw material for forming thin films may be minimized. In an implementation, in the raw material for forming thin films, the number of particles (having a size greater than 0.3 μm) per 1 ml of the liquid-state raw material may be 100 or less, and the number of particles (having a size greater than 0.2 μm) per 1 ml of the liquid-state raw material may be 1000 or less, e.g., 100 or less, when particle measurement in a liquid is performed by a light scattering type particle detector.

In the method of forming the thin film, to fabricate the thin film by using the raw material for forming thin films, a CVD process, in which vapor obtained by vaporizing the raw material for forming thin films and, if desired, a reactive gas, are introduced into a chamber including the substrate placed therein, and the tantalum-containing thin film is grown or deposited on the substrate by performing decomposition and a chemical reaction of the precursor on the substrate, may be performed. Here, a method of supplying the raw material for forming thin films, a deposition method, fabrication conditions, a fabrication apparatus, and the like are not particularly limited, and suitable conditions and methods may be used.

The tantalum compound according to an embodiment may be usefully used for a process of forming a thin film required for fabrication of an integrated circuit device. For example, the tantalum compound may be used as a Ta precursor for a CVD or ALD process.

FIGS. 2A to 2D illustrate schematic diagrams showing configurations of exemplary deposition apparatuses 200A, 200B, 200C, and 200D capable of being used for a process of forming a thin film according to an embodiment.

Each of the deposition apparatuses 200A, 200B, 200C, and 200D shown as examples in FIGS. 2A to 2D includes a fluid transfer unit 210, a thin film forming unit 250 in which a deposition process for forming a thin film on a substrate W is performed by using a process gas supplied from a raw material container 212 in the fluid transfer unit 210, and an exhaust system 270 for discharging gases remaining after use for reaction in the thin film forming unit 250 or discharging reaction by-products.

The thin film forming unit 250 may include a reaction chamber 254 including a susceptor 252 which supports the substrate W. A shower head 256 for supplying a gas supplied by the fluid transfer unit 210 onto the substrate W may be mounted in an upper end portion inside the reaction chamber 254.

The fluid transfer unit 210 may include an inflow line 222 for supplying a carrier gas to the raw material container 212 from the outside of each of the deposition apparatuses, and an outflow line 224 for supplying a raw material compound contained in the raw material container 212 to the thin film forming unit 250. Valves V1 and V2 and mass flow controllers (MFCs) M1 and M2 may be respectively mounted to the inflow line 222 and the outflow line 224. The inflow line 222 and the outflow line 224 may be connected to each other through a bypass line 226. A valve V3 may be mounted to the bypass line 226. The valve V3 may be pneumatically operated by an electric motor or another remote-controllable means.

The raw material supplied from the raw material container 212 may be supplied into the reaction chamber 254 through an inflow line 266 of the thin film forming unit 250, which is connected to the outflow line 224 of the fluid transfer unit 210. The raw material supplied from the raw material container 212 may be supplied into the reaction chamber 254 together with the carrier gas supplied through an inflow line 268, as desired. A valve V4 and an MFC M3 may be mounted to the inflow line 268 through which the carrier gas flows.

The thin film forming unit 250 may include an inflow line 262 for supplying a purge gas into the reaction chamber 254, and an inflow line 264 for supplying a reactive gas into the reaction chamber 254. Valves V5 and V6 and MFCs M4 and M5 may be respectively mounted to the inflow lines 262 and 264.

The used process gas and waste reaction by-products in the reaction chamber 254 may be discharged to the outside of each of the deposition apparatuses through the exhaust system 270. The exhaust system 270 may include an exhaust line 272 connected to the reaction chamber 254, and a vacuum pump 274 mounted to the exhaust line 272. The vacuum pump 274 may remove the process gas and the waste reaction by-products discharged from the reaction chamber 254.

A trap 276 may be mounted to the exhaust line 272 at the upstream side of the vacuum pump 274. The trap 276 may capture the reaction by-products generated by the process gas which has not completely reacted in the reaction chamber, and thus allow the reaction by-products not to flow in the vacuum pump 274 at the downstream side of the trap 276.

In the method of forming the thin film, the tantalum compound represented by General Formula (I) may be used as the raw material compound. In an implementation, the tantalum compound may be present in a liquid state at room temperature (e.g., under ambient conditions) and may react with another process gas, e.g., a reactive gas such as a reductive gas or an oxidative gas. Thus, the trap 276 mounted to the exhaust line 272 may allow the reaction by-products generated due to reaction between the process gases not to flow downstream of the trap 276 by capturing the reaction by-products. The trap 276 may be cooled by a cooler or by water cooling.

In an implementation, a bypass line 278 and an automatic pressure controller 280 may be mounted to the exhaust line 272 at the upstream side of the trap 276. Valves V7 and V8 may be respectively mounted to the bypass line 278 and a portion of the exhaust line 272 extending parallel to the bypass line 278.

Figure 2A:
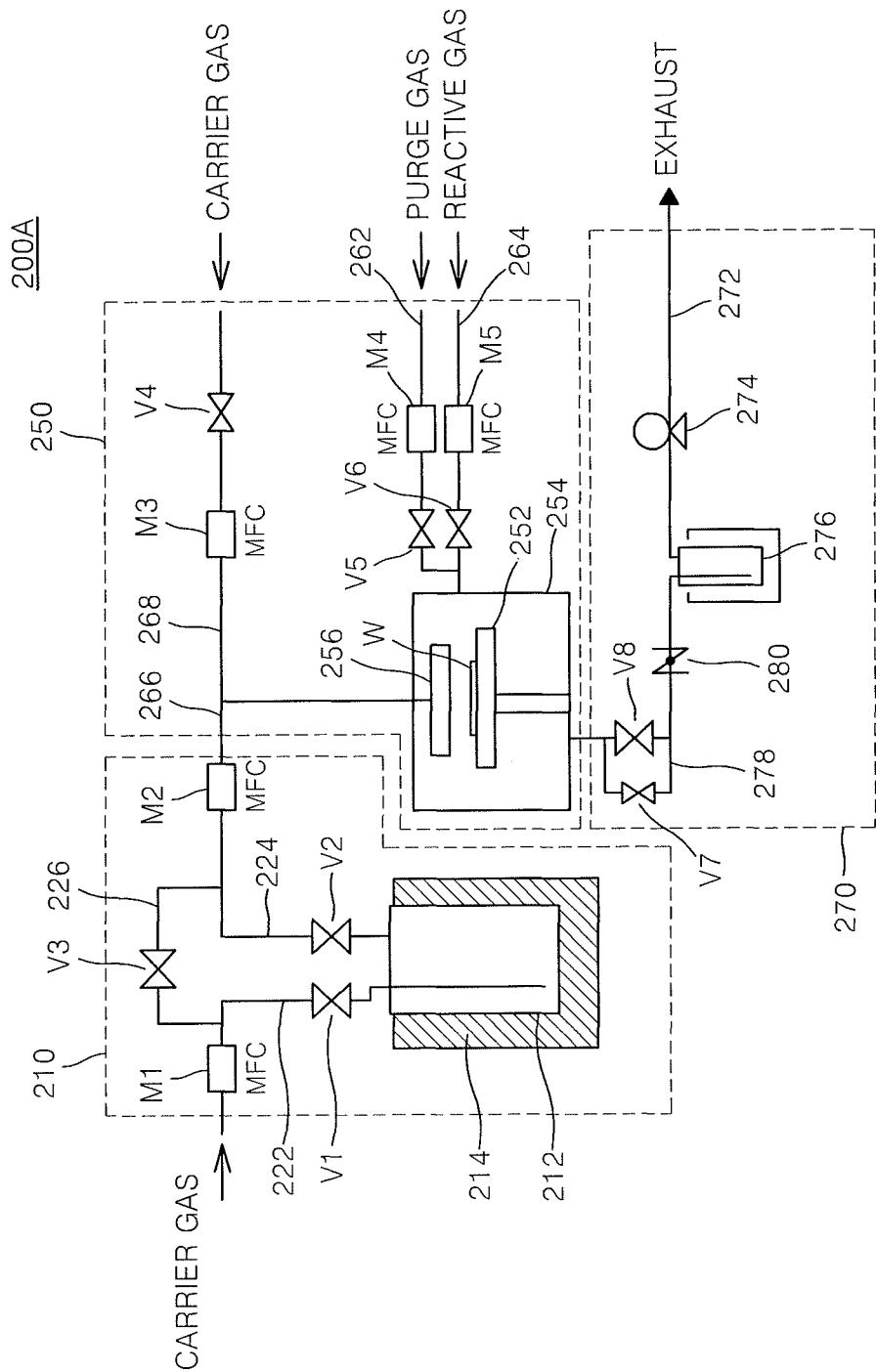
FIGS. 2A to 2D illustrate schematic diagrams of configurations of exemplary deposition apparatuses capable of being used for a process of forming a thin film according to an embodiment.
Figure 2B:
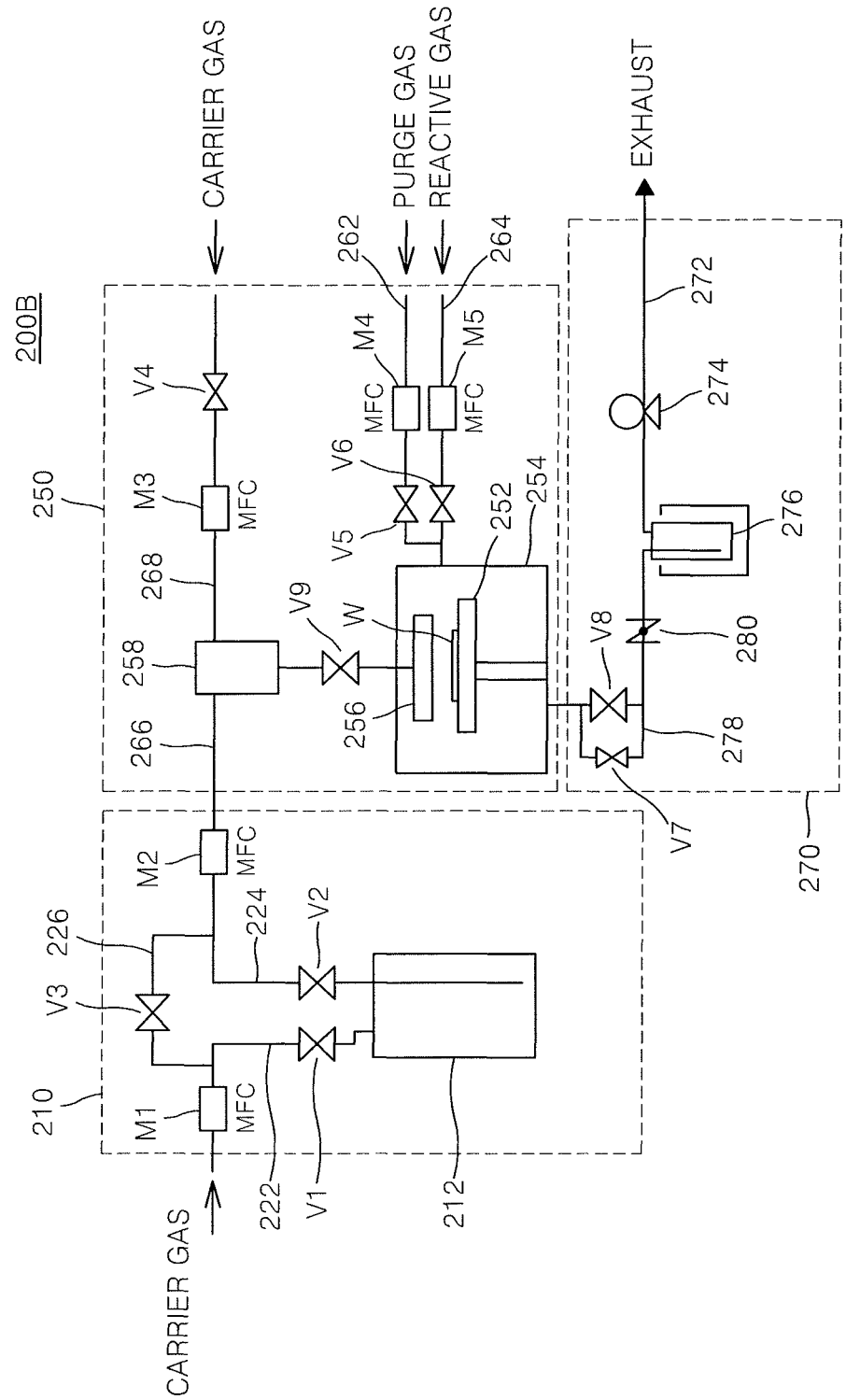
Figure 2C:
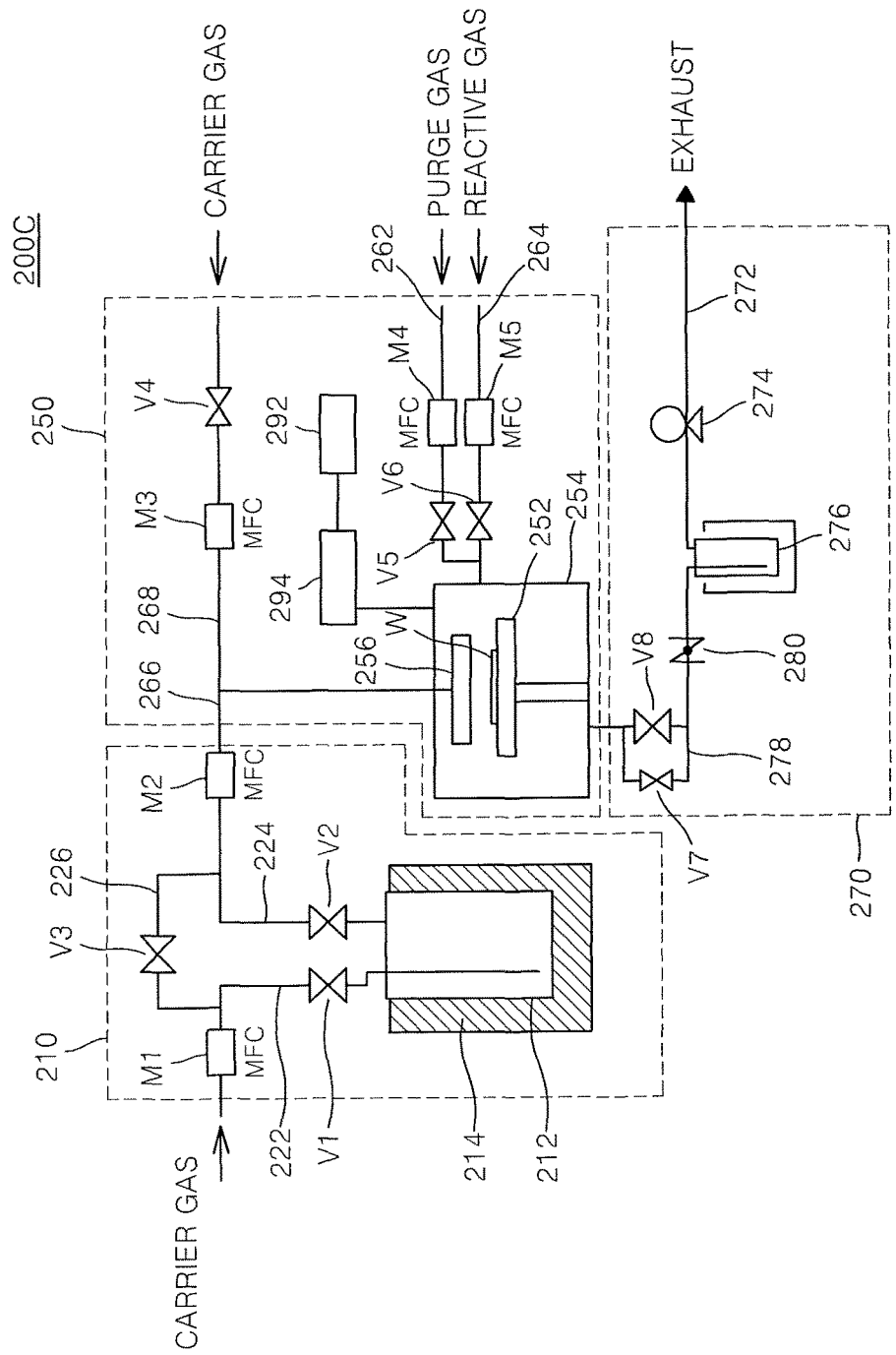

As shown in the deposition apparatuses 200A and 200C in FIGS. 2A and 2C, a heater 214 may be mounted to the raw material container 212. The raw material compound contained in the raw material container 212 may be maintained at a relatively high temperature by the heater 214.

Figure 2D:
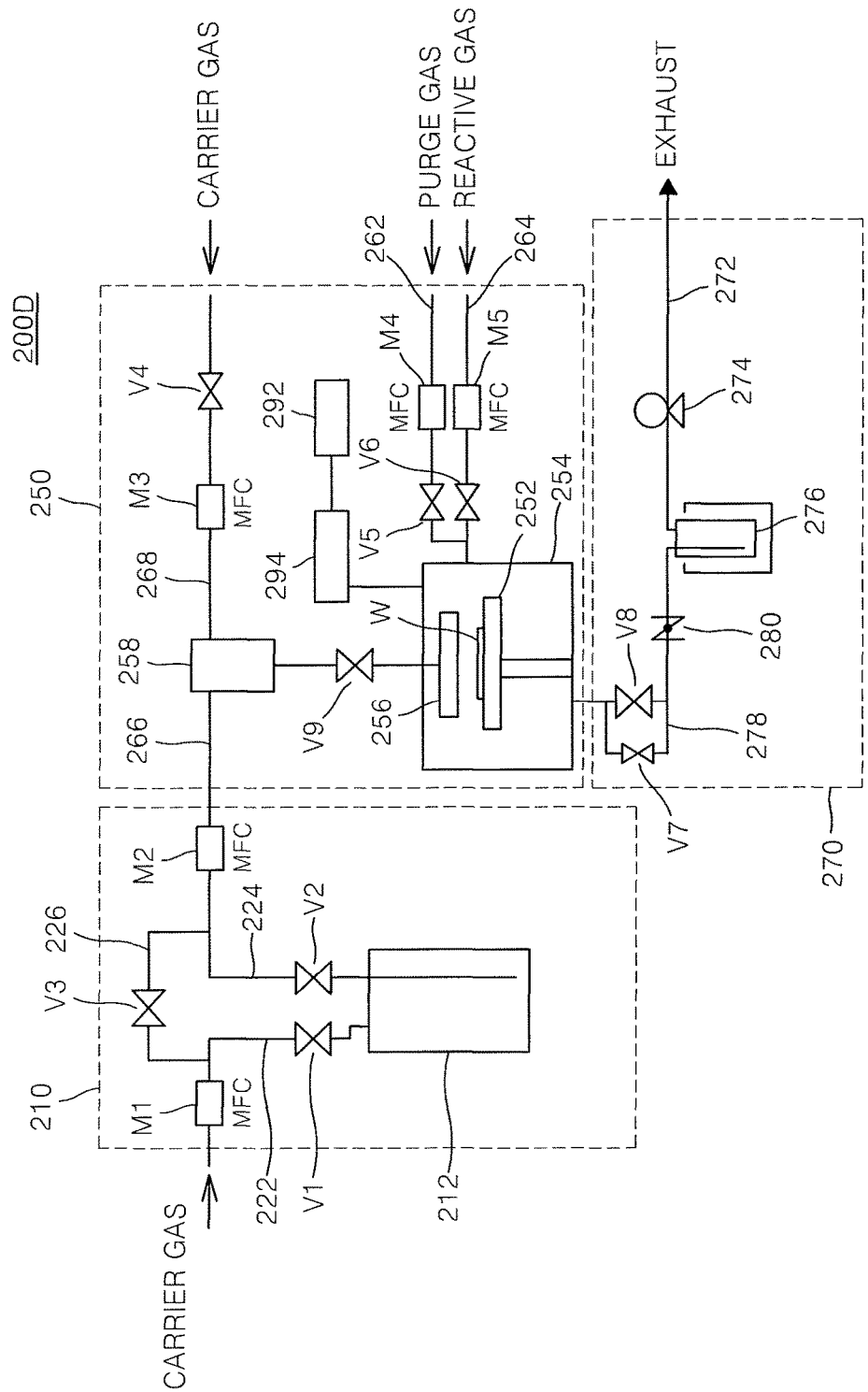

As shown in the deposition apparatuses 200B and 200D in FIGS. 2B and 2D, a vaporizer 258 may be mounted to the inflow line 266 or the thin film forming unit 250. The vaporizer 258 may vaporize a fluid supplied in a liquid state by the fluid transfer unit 210 and supply the vaporized raw material compound into the reaction chamber 254. The raw material compound vaporized in the vaporizer 258 may be supplied into the reaction chamber 254 together with the carrier gas supplied through the inflow line 268. Inflow of the raw material compound supplied into the reaction chamber 254 through the vaporizer 258 may be controlled by a valve V9.

In an implementation, as shown in the deposition apparatuses 200C and 200D in FIGS. 2C and 2D, the thin film forming unit 250 may include a high-frequency power supply 292 and an RF matching system 294 in order to generate plasma inside the reaction chamber 254.

In an implementation, in the deposition apparatuses 200A, 200B, 200C, and 200D in FIGS. 2A to 2D, one raw material container 212 may be connected to the reaction chamber 254. In an implementation, the fluid transfer unit 210 may include a plurality of raw material containers 212 as desired, and each of the plurality of raw material containers 212 may be connected to the reaction chamber 254.

In an implementation, to form the tantalum-containing film on the substrate W according to the method of forming the thin film, one of the deposition apparatuses 200A, 200B, 200C, and 200D shown in FIGS. 2A to 2D may be used.

In an implementation, to form the tantalum-containing film on the substrate according to the process P14 of FIG. 1, the tantalum compound represented by General Formula (I) may be transferred in various methods to be supplied into a reaction chamber of a thin film forming apparatus, e.g., into the reaction chamber 254 of each of the deposition apparatuses 200A, 200B, 200C, and 200D shown in FIGS. 2A to 2D.

In an implementation, to form the thin film by the CVD process using the tantalum compound represented by General Formula (I), the gas transfer method, in which the tantalum compound is vaporized through heating and/or decompression in the raw material container 212, followed by supplying the vaporized tantalum compound into the reaction chamber 254, if desired, together with the carrier gas such as Ar, $N_2$, He, or the like, may be used. When the gas transfer method is used, the tantalum compound itself may be used as the raw material compound for forming thin films in the CVD process.

In an implementation, to form the thin film by the CVD process using the tantalum compound, the liquid transfer method, in which the tantalum compound is transferred in a liquid or solution state to the vaporizer 258, followed by vaporizing the tantalum compound through heating and/or decompression in the vaporizer 258, and then supplied into the reaction chamber 254, may be used. When the liquid transfer method is used, the tantalum compound itself, or a solution in which the tantalum compound is dissolved in an organic solvent may be used as the raw material compound for forming thin films in the CVD process.

In the method of forming the thin film, the tantalum-containing film may be formed in one of the deposition apparatuses 200A, 200B, 200C, and 200D shown in FIGS. 2A to 2D by using the tantalum compound represented by General Formula (I). For this purpose, e.g., to form the tantalum-containing film according to the process P14 of FIG. 1, the tantalum compound may be supplied into the reaction chamber 254 maintained at a temperature of about 100° C. to about 1,000° C. and at a pressure of about 10 Pa to atmospheric or ambient pressure (e.g., about 1 atm). In an implementation, the tantalum compound may be supplied alone onto the substrate W. In an implementation, to form the tantalum-containing film, a multi-component raw material (including a mixture of the tantalum compound and at least one of a precursor compound, a reactive gas, and an organic solvent), may be supplied onto the substrate W. The precursor compound may include a metal that is different from tantalum.

In an implementation, when a tantalum nitride film is formed, the reactive gas may include, e.g., ammonia ($NH_3$), monoalkylamines, dialkylamines, trialkylamines, organic amine compounds, hydrazine compounds, or combinations thereof.

In an implementation, when a tantalum oxide film is formed, the reactive gas may include an oxidative gas, e.g., $O_2$, $O_3$, plasma $O_2$, $H_2O$, $NO_2$, NO, $N_2O$ (nitrous oxide), $CO_2$, $H_2O_2$, HCOOH, $CH_3COOH$, $(CH_3CO)_2O$, or combinations thereof.

In an implementation, the reactive gas may be a reductive gas, e.g., $H_2$.

To transfer the tantalum compound alone or the multi-component raw material which includes the mixture including the tantalum compound, the gas transfer method, the liquid transfer method, the single source method, or the multi-component source method, which is described above, or the like may be used.

In an implementation, to form the tantalum-containing film, a thermal CVD process, in which a raw material gas including the tantalum compound is reacted with a reactive gas only by using heat, a plasma CVD process using heat and plasma, a photo CVD process using heat and light, a photo plasma CVD process using heat, light, and plasma, or an ALD process, in which molecular-level deposition is performed stage by stage by dividing deposition of CVD into basic processes, may be used.

In the method of forming the thin film, the substrate (e.g., the substrate W shown in FIGS. 2A to 2D) for forming the thin film may include: a silicon substrate; a ceramic substrate (such as SiN, TiN, TaN, TiO, RuO, ZrO, HfO, and LaO); a glass substrate; a metal substrate (such as ruthenium), or the like. In an implementation, the substrate may have a shape such as a plate shape, a spherical shape, a fiber shape, or the like. In an implementation, a surface of the substrate may have a planar structure, or a 3-dimensional structure such as a trench structure or the like.

Figure 3:
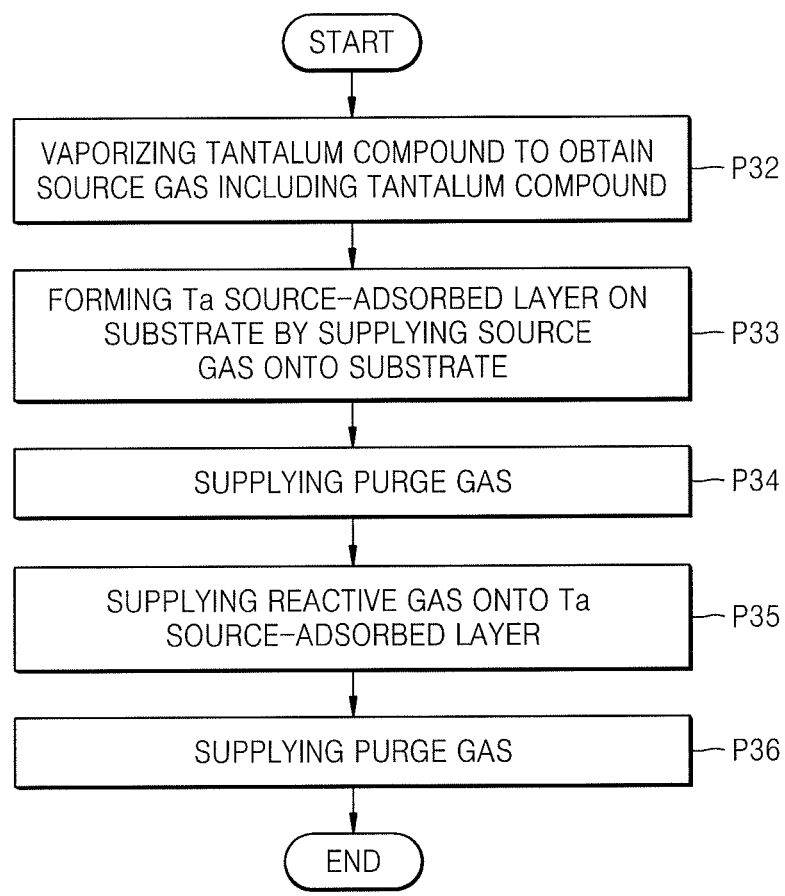
FIG. 3 illustrates a flowchart of an exemplary method of forming a tantalum-containing film, according to embodiments.

FIG. 3 illustrates a flowchart of an exemplary method of forming a tantalum-containing film according to embodiments. The method of forming the tantalum-containing film according to the process P14 of FIG. 1 by using an ALD process will be described with reference to FIG. 3.

Referring to FIG. 3, in a process P32, a source gas including a tantalum compound may be obtained by vaporizing the tantalum compound. The tantalum compound may include the tantalum compound represented by General Formula (I).

In a process P33, a Ta source-adsorbed layer may be formed on a substrate by supplying the source gas obtained according to the process P32 onto the substrate.

In an implementation, the Ta source-adsorbed layer including a chemisorbed layer and a physisorbed layer of the source gas may be formed by supplying the source gas onto the substrate.

In a process P34, unnecessary by-products that may be on the substrate may be removed by supplying a purge gas onto the substrate.

The purge gas may include, e.g., an inert gas such as Ar, He, or Ne, $N_2$ gas, or the like.

In an implementation, the method of forming the tantalum-containing film may further include a process of heating the substrate including the Ta source-adsorbed layer, or a process of heat-treating a reaction chamber containing the substrate. The heat treatment may be performed at a temperature of room temperature to about 400° C., e.g., about 150° C. to about 400° C.

In a process P35, a reactive gas may be supplied onto the Ta source-adsorbed layer formed on the substrate.

In an implementation, when a tantalum nitride film is formed, the reactive gas may include, e.g., $NH_3$, monoalkylamines, dialkylamines, trialkylamines, organic amine compounds, hydrazine compounds, or combinations thereof.

In an implementation, when a tantalum oxide film is formed, the reactive gas may be an oxidative gas, e.g., $O_2$, $O_3$, plasma $O_2$, $H_2O$, $NO_2$, NO, $N_2O$ (nitrous oxide), $CO_2$, $H_2O_2$, HCOOH, $CH_3COOH$, $(CH_3CO)_2O$, or combinations thereof.

In an implementation, the reactive gas may be a reductive or reducing gas, e.g., $H_2$.

In a process P36, unnecessary by-products that may be on the substrate may be removed by supplying a purge gas onto the substrate.

The purge gas may include, e.g., an inert gas such as Ar, He, or Ne, $N_2$ gas, or the like.

In an implementation, to form the tantalum-containing film, the tantalum compound represented by General Formula (I), and at least one of another precursor, a reactive gas, a carrier gas, and a purge gas may be simultaneously or sequentially supplied onto the substrate. Details of the other precursor, the reactive gas, the carrier gas, and the purge gas, which may be supplied onto the substrate together with the tantalum compound represented by General Formula (I), may be the same as described above.

To form the tantalum-containing film according to the processes of FIGS. 1 and 3, the tantalum compound represented by General Formula (I) may be transferred in various methods to be supplied into a reaction chamber of a thin film forming apparatus, e.g., into the reaction chamber 254 of each of the deposition apparatuses 200A, 200B, 200C, 200D shown in FIGS. 2A to 2D.

In the method of forming the thin film, conditions for forming the tantalum-containing film may include a reaction temperature (substrate temperature), a reaction pressure, a deposition rate, or the like.

The reaction temperature may be a temperature at which the tantalum compound, e.g., the tantalum compound represented by General Formula (I), may sufficiently react. In an implementation, the reaction temperature may be a temperature of about 100° C. or more, e.g., about 150° C. to about 400° C. or about 150° C. to about 250° C.

In an implementation, the reaction pressure may range from about 10 Pa to atmospheric pressure when a thermal CVD or photo CVD process is used, and may range from about 10 Pa to about 2000 Pa when plasma CVD is used.

In an implementation, the deposition rate may be controlled by controlling conditions for supplying a raw material compound (e.g., a vaporization temperature and a vaporization pressure), the reaction temperature, or the reaction pressure. In an implementation, in the method of forming the thin film, the deposition rate of the tantalum-containing film may range from about 0.01 nm/min to about 100 nm/min, e.g., from about 1 nm/min to about 50 nm/min.

When the tantalum-containing film is formed by using the ALD process, the number of ALD cycles may be adjusted in order to control the tantalum-containing film to a desired thickness.

When the tantalum-containing film is formed by using the ALD process, energy such as plasma, light, voltage, or the like may be applied. A time point for applying the energy may be variously selected. For example, at a time point at which the source gas including the tantalum compound is introduced into the reaction chamber, at a time point at which the source gas is adsorbed onto the substrate, at a time point at which an exhaust process is performed by using the purge gas, at a time point at which the reactive gas is introduced into the reaction chamber, or between these time points, the energy such as plasma, light, voltage, or the like may be applied.

In an implementation, the method of forming the thin film may further include a process of annealing the tantalum-containing film under an inert, oxidative, or reductive atmosphere, after the tantalum-containing film is formed by using the tantalum compound represented by General Formula (I). In an implementation, to fill a step formed on a surface of the tantalum-containing film, the method of forming the thin film may further include a process of reflowing the tantalum-containing film, as desired. In an implementation, each of the annealing process and the reflow process may be performed at a temperature of about 200° C. to about 1,000° C., e.g., about 250° C. to about 1,000° C.

In an implementation, the method of forming the thin film as described with reference to FIGS. 1 and 3 may be performed by using the deposition apparatuses 200A, 200B, 200C, and 200D as shown in FIGS. 2A to 2D. In an implementation, the method of forming the thin film as described with reference to FIGS. 1 and 3 may be performed by using a batch-type apparatus instead of a single-type apparatus such as the deposition apparatuses 200A, 200B, 200C, and 200D shown in FIGS. 2A to 2D, thereby simultaneously forming the tantalum-containing film on a large number of substrates.

According to the method of forming the thin film, the tantalum compound, the other precursor used together with the tantalum compound, the reactive gas, and the conditions for forming the thin film may be appropriately selected, thereby forming various tantalum-containing films. In an implementation, the tantalum-containing film, which is formed by the method of forming the thin film, may include, e.g., a tantalum nitride film, a tantalum oxide film, or a (e.g., metallic) tantalum film.

Different-component precursors, the reactive gas, and the conditions for forming the thin film may be appropriately selected, whereby the thin film fabricated by using the raw material for forming thin films, which includes the tantalum compound according to an embodiment, may be provided as a desired thin film such as a metal, an oxide ceramic, a nitride ceramic, glass, or the like. In an implementation, the thin film fabricated by using the raw material for forming thin films, which includes the tantalum compound, may include, e.g., a tantalum nitride film represented by TaN, a tantalum oxide film represented by $Ta_2O_3$, a Ta thin film, a composite oxide thin film of Ta and Al, a composite oxide thin film of Ta, Zr, and Hf, a composite oxide thin film of Ta, Si, Zr, and Hf, a composite oxide thin film of Ta, La, and Nb, a composite oxide thin film of Ta, Si, La, and Nb, a Ta-doped ferroelectric composite oxide thin film, a Ta-doped glass thin film, or the like.

The tantalum-containing film fabricated by the method of forming the thin film may be used for various purposes. For example, the tantalum-containing film may be used for a gate of a transistor, a conductive barrier film used for a metal wire, e.g., a copper wire, a dielectric film of a capacitor, a barrier metal film for liquid crystals, a member for thin film solar cells, a member for semiconductor equipment, a nanostructure, or the like.

Figure 4A:
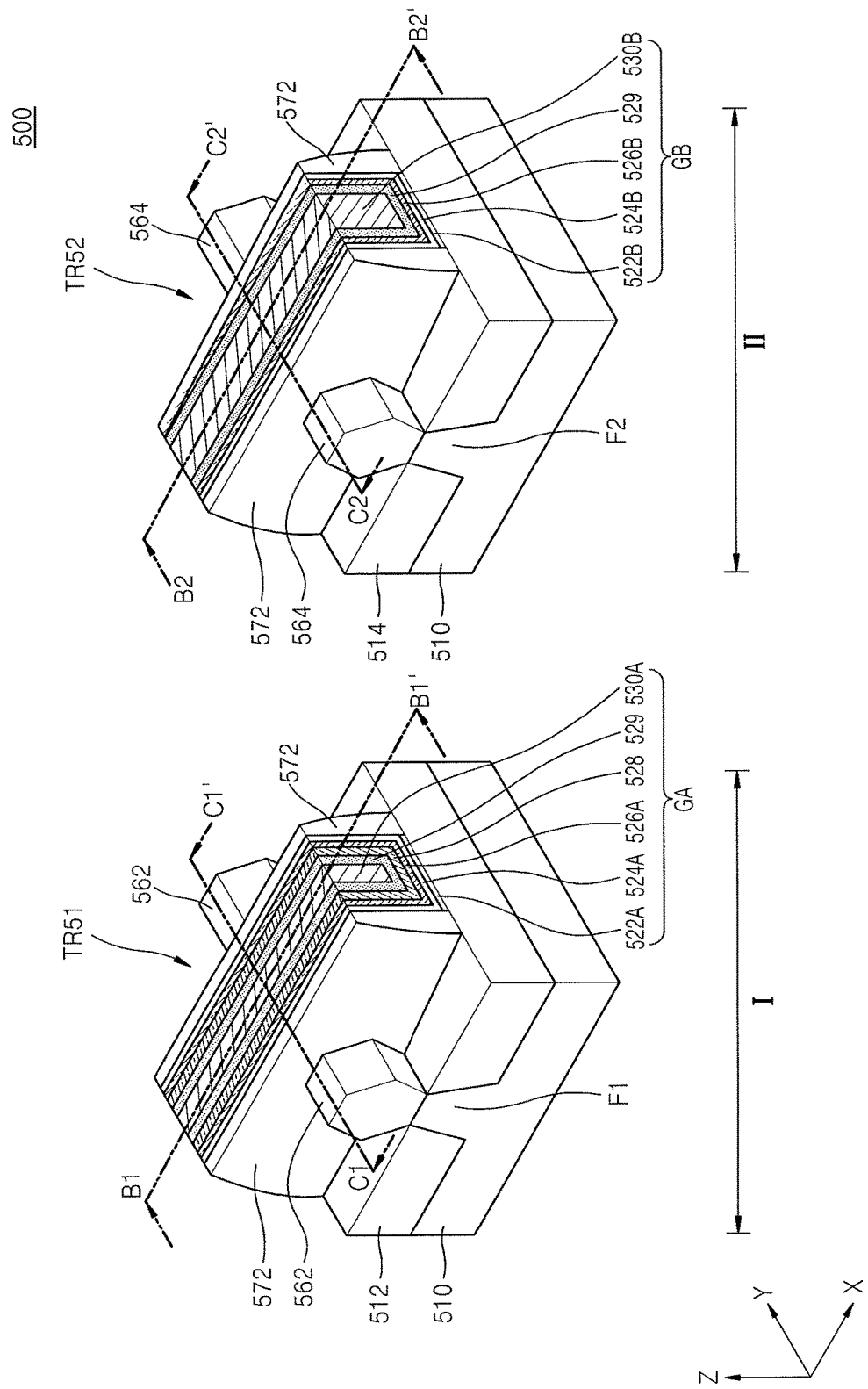
FIGS. 4A to 4C illustrate diagrams showing an integrated circuit device according to embodiments.
Figure 4B:
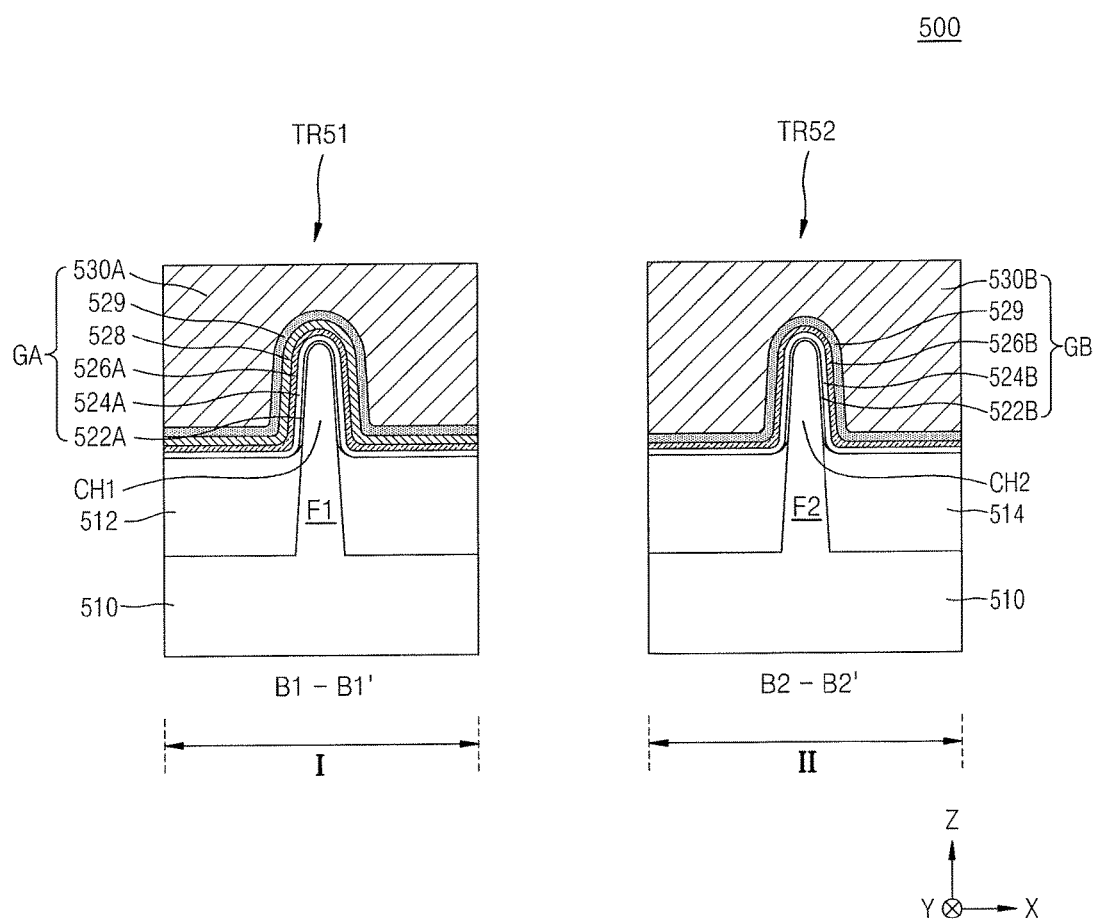
Figure 4C:
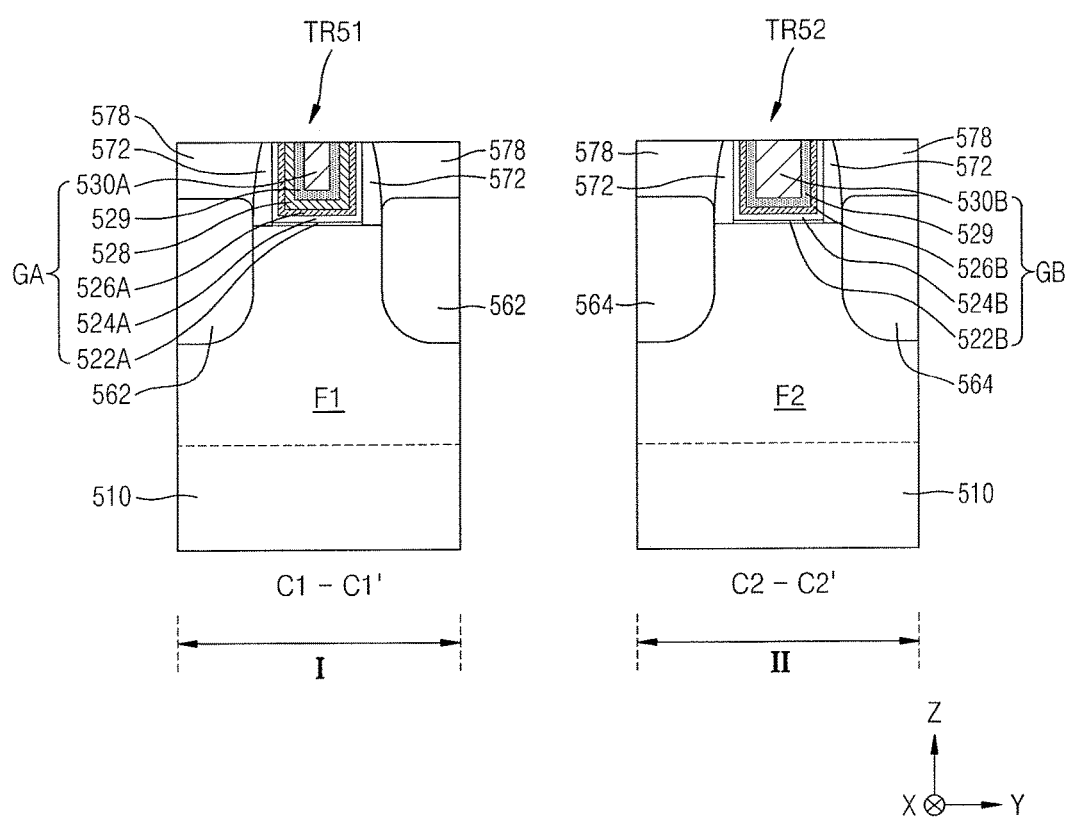

FIGS. 4A to 4C illustrate diagrams for explaining an integrated circuit device according to embodiments. FIG. 4A shows perspective views of main components of an integrated circuit device 500 which includes first and second transistors TR51 and TR52 having FinFET structures, FIG. 4B shows cross-sectional views taken along lines B1-B1' and B2-B2' of FIG. 4A, and FIG. 4C shows cross-sectional views taken along lines C1-C1' and C2-C2' of FIG. 4A.

The integrated circuit device 500 may include a first fin-type (e.g., fin-shaped) active region F1 and a second fin-type active region F2, which respectively protrude from a first region I and a second region II of a substrate 510 in a direction (Z direction) perpendicular to a main plane of the substrate 510.

The first region I and the second region II refer to different regions of the substrate 510 and may be regions performing different functions on the substrate 510. The first transistor TR51 and the second transistor TR52, which require different threshold voltages, may be respectively formed in the first region I and the second region II. In an implementation, the first region I may be a PMOS transistor region, and the second region II may be an NMOS transistor region.

The first fin-type active region F1 and the second fin-type active region F2 may extend along one direction (Y direction in FIGS. 4A to 4C). In the first region I and the second region II, a first device isolation film 512 and a second device isolation film 514, which respectively cover lower sidewalls of the first fin-type active region F1 and the second fin-type active region F2, are formed on the substrate 510. The first fin-type active region F1 protrudes in a fin shape upwards from the first device isolation film 512, and the second fin-type active region F2 protrudes in a fin shape upwards from the second device isolation film 514.

The first fin-type active region F1 and the second fin-type active region F2 may respectively have a first channel region CH1 and a second channel region CH2 on upper sides thereof. A P-type channel is formed in the first channel region CH1 and an N-type channel is formed in the second channel region CH2.

In an implementation, each of the first fin-type active region F1 and the second fin-type active region F2 may include a single material. In an implementation, the first fin-type active region F1 and the second fin-type active region F2, which respectively include the first channel region CH1 and the second channel region CH2, may include Si in all regions thereof. In an implementation, the first fin-type active region F1 and the second fin-type active region F2 may respectively include a region including Ge and a region including Si.

Each of the first and second device isolation films 512 and 514 may include a silicon-containing insulating film, such as a silicon oxide film, a silicon nitride film, a silicon oxynitride film, a silicon carbonitride film, or the like, polysilicon, or combinations thereof.

In the first region I, a first gate structure GA may extend on the first fin-type active region F1 in a direction (X direction in FIGS. 4A to 4C) intersecting with the extension direction of the first fin-type active region F1, the first gate structure GA including a first interface film 522A, a first high-K dielectric film 524A, a first etch stop layer 526A, a first work function adjusting layer 528, a second work function adjusting layer 529, and a first gap-fill gate film 530A, which are sequentially stacked. The first transistor TR51 is formed at a point at which the first fin-type active region F1 intersects with the first gate structure GA.

In the second region II, a second gate structure GB may extend on the second fin-type active region F2 in the direction (X direction in FIGS. 4A to 4C) intersecting with the extension direction of the second fin-type active region F2, the second gate structure GB including a second interface film 522B, a second high-K dielectric film 524B, a second etch stop layer 526B, the second work function adjusting layer 529, and a second gap-fill gate film 530B, which are sequentially stacked. The second transistor TR52 may be formed at a point at which the second fin-type active region F2 intersects with the second gate structure GB.

The first interface film 522A and the second interface film 522B may include films obtained by oxidizing surfaces of a first fin-type active region F1 and a second fin-type active region F2, respectively. In an implementation, each of the first interface film 522A and the second interface film 522B may include a low-K material layer having a dielectric constant of about 9 or less, e.g., a silicon oxide film, a silicon oxynitride film, or combinations thereof. In an implementation, each of the first interface film 522A and the second interface film 522B may have a thickness of, e.g., about 5 Å to about 20 Å. In an implementation, the first interface film 522A and/or the second interface film 522B may be omitted.

Each of the first high-K dielectric film 524A and the second high-K dielectric film 524B may include a metal oxide having a higher dielectric constant than a silicon oxide film. In an implementation, each of the first high-K dielectric film 524A and the second high-K dielectric film 524B may have a dielectric constant of about 10 to 25. Each of the first high-K dielectric film 524A and the second high-K dielectric film 524B may include, e.g., hafnium oxide, hafnium oxynitride, hafnium silicon oxide, lanthanum oxide, lanthanum aluminum oxide, zirconium oxide, zirconium silicon oxide, tantalum oxide, titanium oxide, barium strontium titanium oxide, barium titanium oxide, strontium titanium oxide, yttrium oxide, aluminum oxide, lead scandium tantalum oxide, lead zinc niobate, or combinations thereof.

The first high-K dielectric film 524A and the second high-K dielectric film 524B may be formed by an ALD or CVD process. Each of the first high-K dielectric film 524A and the second high-K dielectric film 524B may have a thickness of, e.g., about 10 Å to about 40 Å.

When each of the first high-K dielectric film 524A and the second high-K dielectric film 524B includes a Ta-containing film, the first high-K dielectric film 524A and/or the second high-K dielectric film 524B may be formed by using the thin film forming raw material, which includes the tantalum compound represented by General Formula (I) as set forth above.

In an implementation, each of the first etch stop layer 526A and the second etch stop layer 526B may include a TaN film. In an implementation, the first etch stop layer 526A and/or the second etch stop layer 526B may be formed by a CVD or ALD process by using the thin film forming raw material, which includes the tantalum compound represented by General Formula (I) as set forth above, and using a nitrogen atom-containing reactive gas, e.g., $NH_3$ gas.

The first work function adjusting layer 528 may be for adjusting a work function of the P-type transistor, and may include, e.g., TiN.

The second work function adjusting layer 529 may be for adjusting a work function of the N-type transistor, and may include, e.g., TiAl, TiAlC, TiAlN, TaC, TiC, HfSi, or combinations thereof.

Each of the first gap-fill gate film 530A and the second gap-fill gate film 530B may include, e.g., W.

In an implementation, a conductive barrier film may be interposed between the second work function adjusting layer 529 and the first gap-fill gate film 530A, and/or between the second work function adjusting layer 529 and the second gap-fill gate film 530B. In an implementation, the conductive barrier film may include a metal nitride, e.g., TiN, TaN, or combinations thereof.

A pair of first source/drain regions 562 may be formed in the first fin-type active region F1 at both sides of the first gate structure GA. A pair of second source/drain regions 564 may be formed in the second fin-type active region F2 at both sides of the second gate structure GB.

The pairs of first and second source/drain regions 562 and 564 may respectively include semiconductor layers epitaxially grown on the first and second fin-type active regions F1 and F2. Each of the pairs of first and second source/drain regions 562 and 564 may include an embedded SiGe structure including a plurality of epitaxially grown SiGe layers, an epitaxially grown Si layer, or an epitaxially grown SiC layer.

In an implementation, the pairs of first and second source/drain regions 562 and 564 may have various suitable sectional shapes.

Each of the first and second transistors TR51 and TR52 may include a 3-dimensional structured MOS transistor in which a channel is formed on an upper surface and both side surfaces of each of the first and second fin-type active regions F1 and F2. The MOS transistor may constitute an NMOS transistor or a PMOS transistor.

In the first region I and the second region II, an insulating spacer 572 may be formed on both sides of each of the first and second gate structures GA and GB. In an implementation, as shown in FIG. 4C, an insulating layer 578 covering the insulating spacer 572 may be formed at an opposite side to each of the first and second gate structures GA and GB, with the insulating spacer 572 being between each of the first and second gate structures GA and GB and the insulating layer 578. The insulating spacer 572 may include a silicon oxide film, and the insulating layer 578 may include a silicon oxide film.

FIGS. 5A to 5H illustrate cross-sectional views of stages in a method of fabricating an integrated circuit device according to embodiments. A method of fabricating the integrated circuit device 500 shown in FIGS. 4A to 4C will be described with reference to FIGS. 5A to 5H. In FIGS. 5A to 5H, the same reference numerals as in FIGS. 4A to 4C denote the same members, and details thereof may be omitted.

Figure 5A:
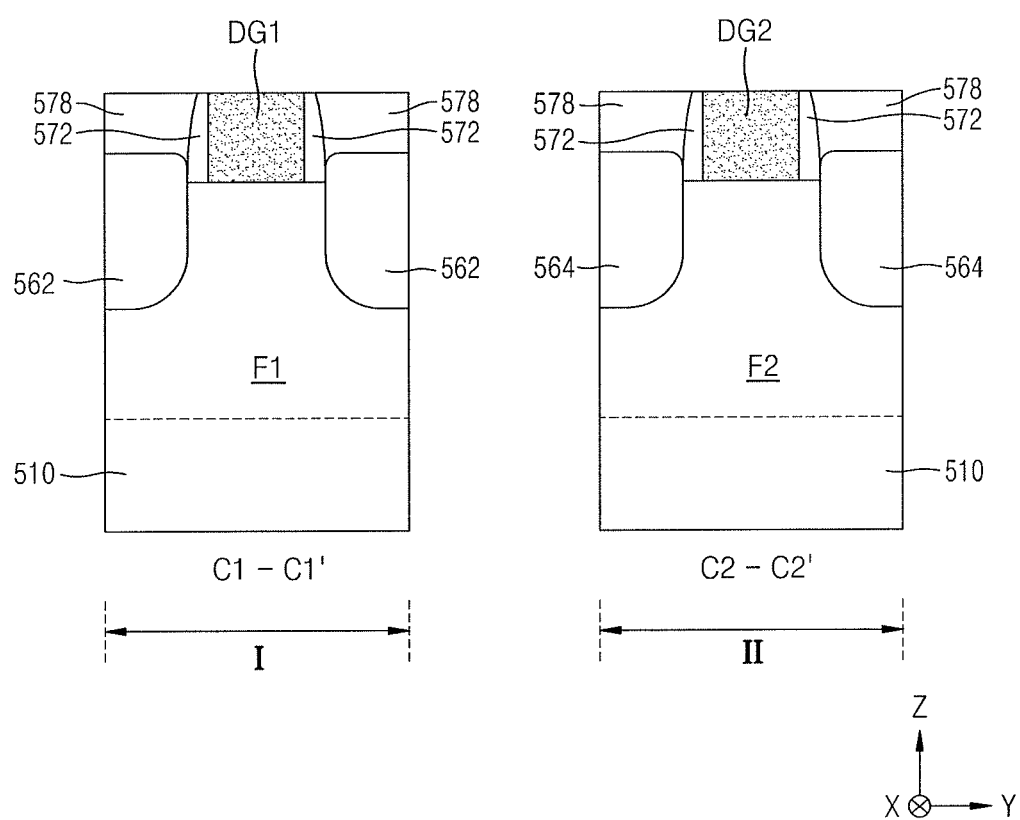
FIGS. 5A to 5H illustrate cross-sectional views of stages in a method of fabricating an integrated circuit device according to embodiments.

Referring to FIG. 5A, the substrate 510 including the first region I and the second region II is prepared.

The substrate 510 may include a semiconductor such as Si or Ge, or a compound semiconductor such as SiGe, SiC, GaAs, InAs, or InP. In an implementation, the substrate 510 may include at least one of a Group III-V material and a Group IV material. The Group III-V material may be a binary, ternary, or quaternary compound including at least one Group III element and at least one Group V element. The Group III-V material may be a compound including at least one element of In, Ga, and Al as a Group III element, and at least one element of As, P, and Sb as a Group V element. In an implementation, the Group III-V material may be selected from among, e.g., InP, $In_zGa_{1-z}As$ ($0 \leq z \leq 1$), and $Al_zGa_{1-z}As$ ($0 \leq z \leq 1$). The binary compound may be, e.g., one of InP, GaAs, InAs, InSb, and GaSb. The ternary compound may be one of, e.g., InGaP, InGaAs, AlInAs, InGaSb, GaAsSb, and GaAsP. The Group IV material may be, e.g., Si or Ge. The Group III-V material and the Group IV material such as Ge may be used as a channel material allowing a low-power high-speed transistor to be made. A high-performance CMOS may be formed by using a semiconductor substrate including a Group III-V material, e.g., GaAs, which has a higher electron mobility than Si, and using a semiconductor substrate including a semiconductor material, e.g., Ge, which has a higher hole mobility than Si. In an implementation, when an NMOS transistor is formed on the substrate 510, the substrate 510 may include one of the exemplary Group II I-V materials set forth above. In an implementation, when a PMOS transistor is formed on the substrate 510, at least a portion of the substrate 510 may include Ge. In an implementation, the substrate 510 may have a silicon on insulator (SOI) structure. The substrate 510 may include a conductive region, e.g., an impurity-doped well, or an impurity-doped structure.

A plurality of trenches may be formed in the first region I and the second region II of the substrate 510 by etching some regions of the substrate 510, thereby forming the first and second fin-type active regions F1 and F2, which protrude upwards from the substrate 510 along a direction (Z direction) perpendicular to the main plane of the substrate 510, and extend in one direction (Y direction). In addition, the first device isolation film 512 and the second device isolation film 514, which respectively cover lower sidewalls of the first and second fin-type active regions F1 and F2, are formed in the plurality of trenches.

Next, in the first region I and the second region II, a first dummy gate DG1 and a second dummy gate DG2 may be respectively formed on upper sides of the first and second fin-type active regions F1 and F2 and upper sides of the first and second device isolation films 512 and 514, and the insulating spacers 572 and the pairs of first and second source/drain regions 562 and 564 are respectively formed at both sides of the first dummy gate DG1 and the second dummy gate DG2. Next, the insulating film 578 may cover each of the pairs of first and second source/drain regions 562 and 564.

Each of the first dummy gate DG1 and the second dummy gate DG2 may include polysilicon.

Figure 5B:
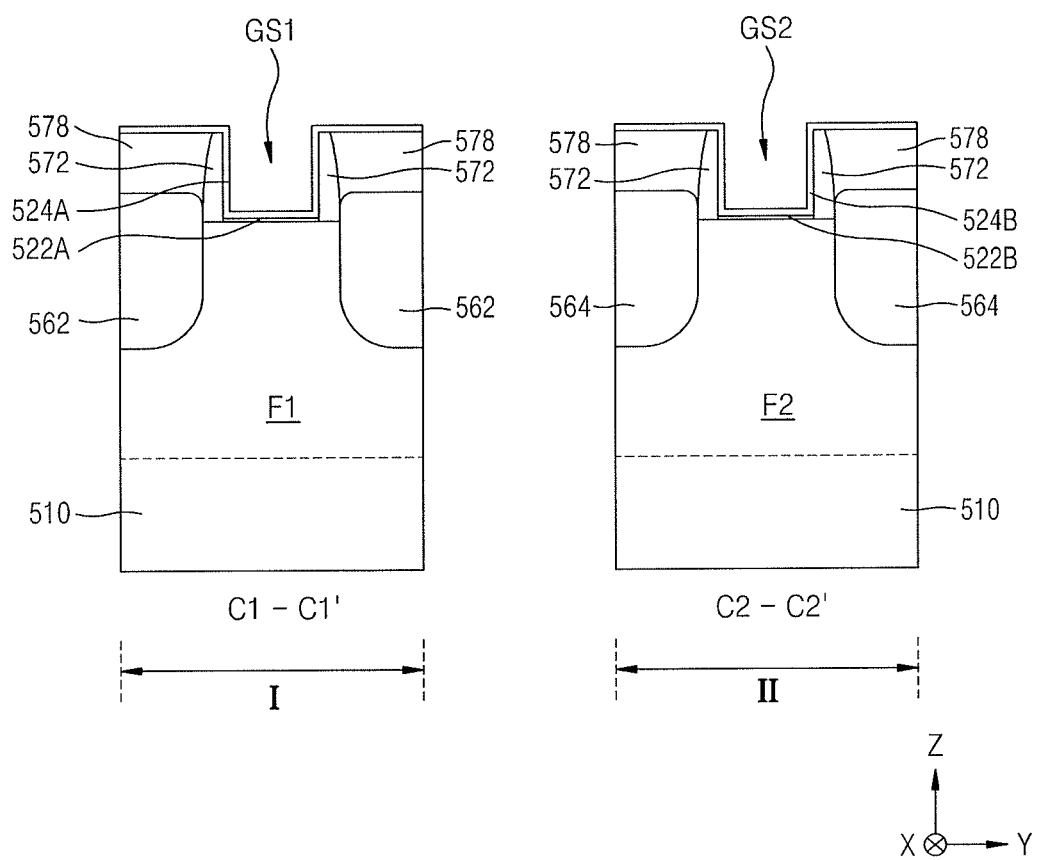

Referring to FIG. 5B, in the first region I and the second region II, a first gate space GS1 and a second gate space GS2 are respectively emptied by removing the first dummy gate DG1 and the second dummy gate DG2. Next, the first interface film 522A is formed on an exposed surface of the first fin-type active region F1 within the first gate space GS1, and the second interface film 522B is formed on an exposed surface of the second fin-type active region F2 within the second gate space GS2.

Next, the first high-K dielectric film 524A and the second high-K dielectric film 524B, which respectively cover exposed surfaces of the first region I and the second region II, are formed. The first high-K dielectric film 524A may conformally cover the first interface film 522A exposed on a bottom surface of the first gate space GS1 and the insulating spacer 572 exposed on sidewalls of the first gate space GS1. The second high-K dielectric film 524B may conformally cover the second interface film 522B exposed on a bottom surface of the second gate space GS2 and the insulating spacer 572 exposed on sidewalls of the second gate space GS2.

The first high-K dielectric film 524A and the second high-K dielectric film 524B may be simultaneously formed. The first high-K dielectric film 524A and the second high-K dielectric film 524B may include the same material.

Figure 5C:
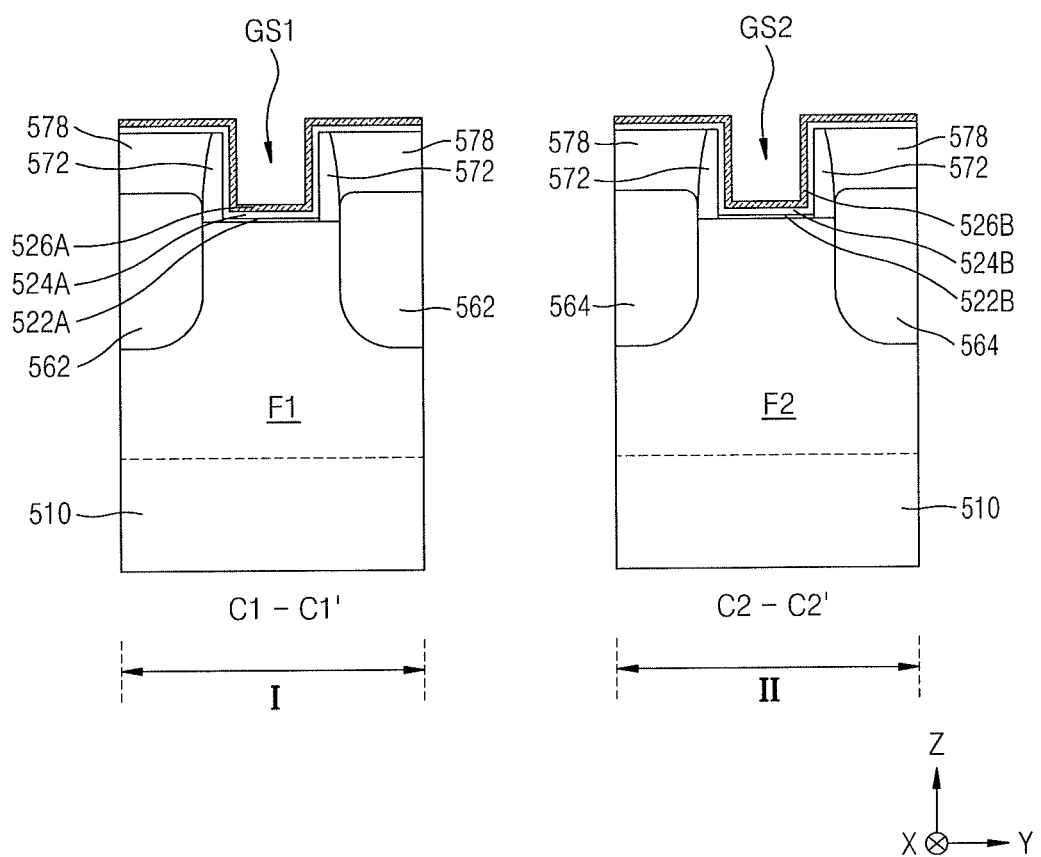

Referring to FIG. 5C, the first etch stop layer 526A covering the first high-K dielectric film 524A in the first region I, and the second etch stop layer 526B covering the second high-K dielectric film 524B in the second region II may be formed.

Each of the first etch stop layer 526A and the second etch stop layer 526B may include a TaN film. In an implementation, the first etch stop layer 526A and the second etch stop layer 526B may be formed by the method of forming the thin film as described with reference to FIGS. 1 and 3 by using the thin film forming raw material, which includes the tantalum compound represented by General Formula (I) as set forth above, and using a nitrogen atom-containing reactive gas, for example, $NH_3$ gas.

In an implementation, a CVD process may be used to form the first etch stop layer 526A and the second etch stop layer 526B. In an implementation, to form the first etch stop layer 526A and the second etch stop layer 526B, the tantalum compound represented by General Formula (I) and the nitrogen atom-containing reactive gas may be simultaneously supplied onto the first etch stop layer 526A and the second etch stop layer 526B.

In an implementation, an ALD process may be used to form the first etch stop layer 526A and the second etch stop layer 526B. In an implementation, to form the first etch stop layer 526A and the second etch stop layer 526B, a first process of forming a tantalum compound-adsorbed layer on the first high-K dielectric film 524A and the second high-K dielectric film 524B by supplying the tantalum compound represented by General Formula (I) onto the high-K dielectric films, a second process of removing unnecessary by-products that may be on the substrate 510 by using a purge gas, e.g., Ar, a third process of reacting the tantalum compound-adsorbed layer with the nitrogen atom-containing reactive gas by supplying the reactive gas onto the tantalum compound-adsorbed layer, and a fourth process of removing unnecessary by-products that may be on the substrate 510 by using a purge gas, e.g., Ar, may be performed. In an implementation, the first to fourth processes may be sequentially repeated a plurality of times until the first etch stop layer 526A and the second etch stop layer 526B having desired thicknesses are obtained.

In an implementation, the tantalum compound represented by General Formula (I) may be a liquid at room temperature and ambient pressure. For example, the tantalum compound may have a relatively low melting point, and can be delivered in a liquid state. In an implementation, the tantalum compound may be easily vaporized due to a relatively high vapor pressure thereof, and delivery of the tantalum compound may be facilitated. Therefore, the tantalum compound may be suitable for being used as a precursor for forming the tantalum-containing film in a deposition process, such as ALD, CVD, or the like, in which the raw material compound is supplied in a vaporized state. For example, the tantalum compound may be easily transferred to a structure having a relatively high aspect ratio due to the relatively high vapor pressure thereof, and the tantalum-containing film exhibiting good step coverage may be formed on the structure having a relatively high aspect ratio.

Figure 5D:
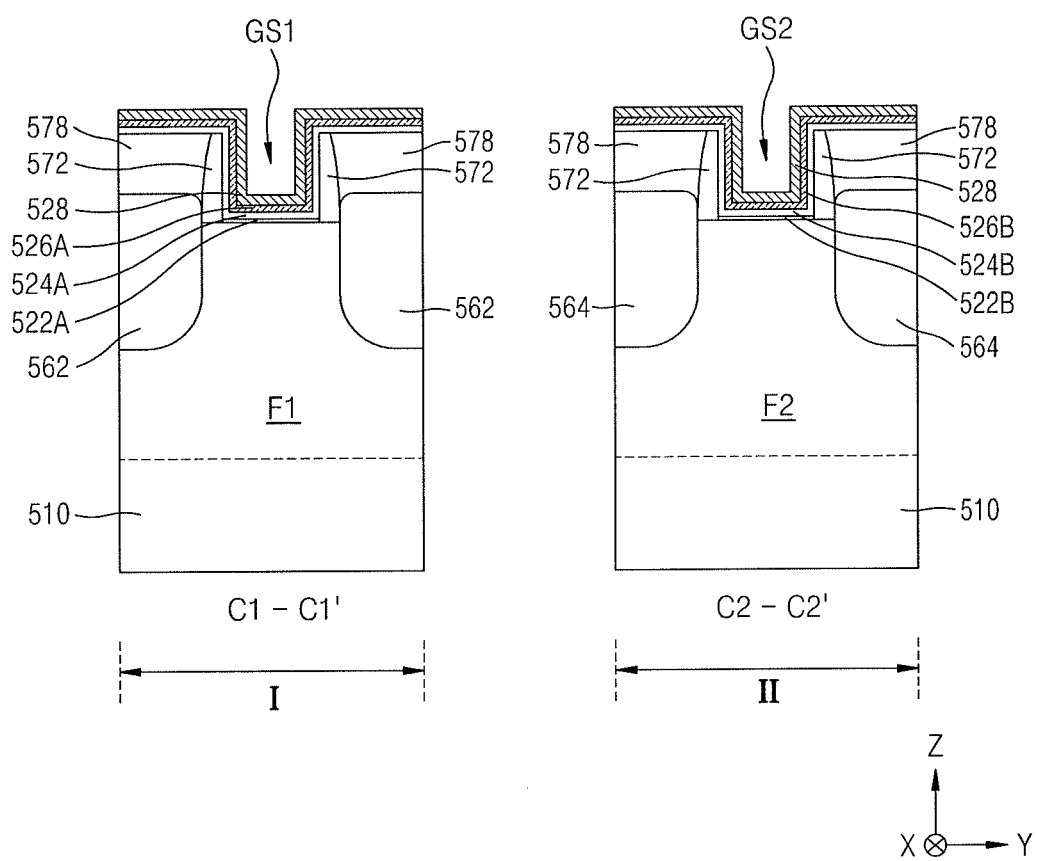

Referring to FIG. 5D, in the first region I and the second region II, the first work function adjusting layer 528 may be formed on the first etch stop layer 526A and the second etch stop layer 526B.

In an implementation, the first work function adjusting layer 528 may include, e.g., TiN.

Figure 5E:
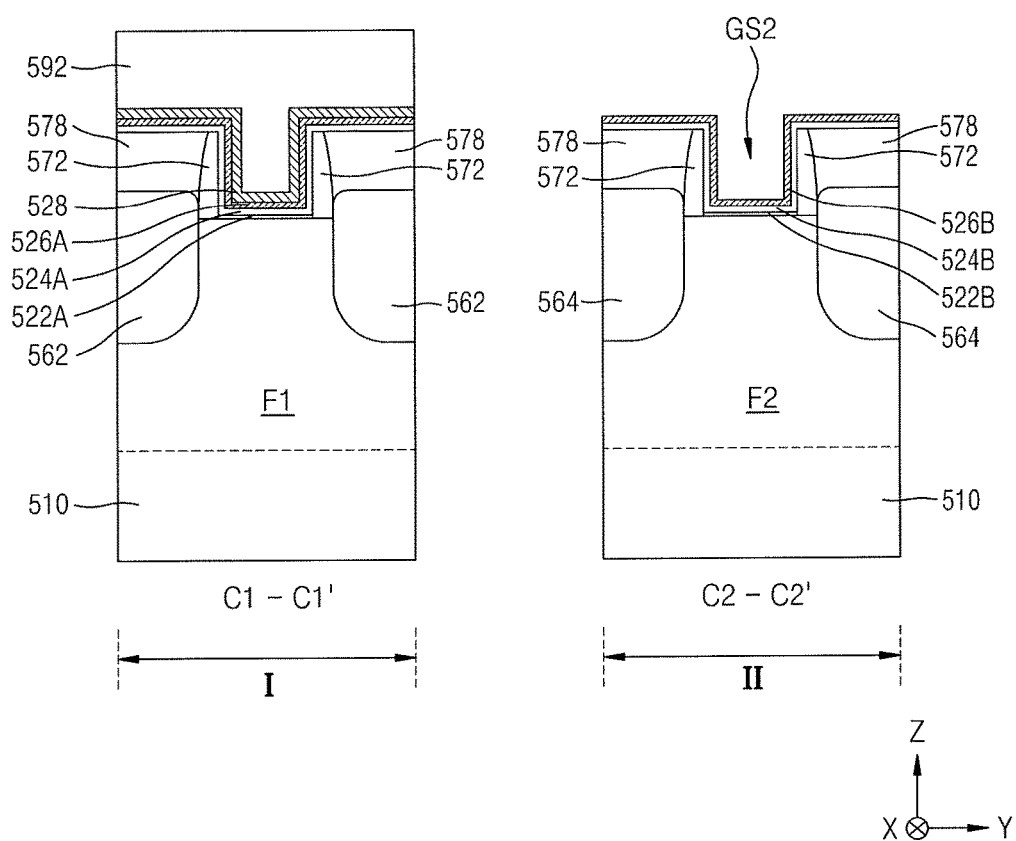

Referring to FIG. 5E, a mask pattern 592 may be formed on the first region I such that the mask pattern 592 covers the first work function adjusting layer 528 in the first region I while exposing the first work function adjusting layer 528 in the second region II. Next, the second etch stop layer 526B may be exposed by removing the first work function adjusting layer 528 in the second region II by using the mask pattern 592 as an etch mask.

To remove the first work function adjusting layer 528 in the second region II, a wet or dry etching process may be used. In an implementation, to remove the first work function adjusting layer 528, an etching process using an etch solution including $H_2O_2$ may be performed. In an implementation, the second etch stop layer 526B may be a film formed by using the thin film forming raw material including the tantalum compound represented by General Formula (I) as set forth above, and may have excellent etch resistance to the etch solution including $H_2O_2$. For example, even though the second etch stop layer 526B may be exposed to $H_2O_2$ included in the etch solution after the first work function adjusting layer 528 is removed by using the etch solution including $H_2O_2$, the second etch stop layer 526B may not be damaged by $H_2O_2$ or may not suffer from a change of composition, and may have strong resistance to oxygen atom penetration.

In contrast, if a TaN film were to be formed by using a different precursor, e.g. pentakis(dimethylamino)Ta (PDMAT), as a Ta source in order to form the second etch stop layer 526B including the TaN, when the TaN film formed by using PDMAT is exposed to the etch solution including $H_2O_2$, the exposed TaN film may be changed into a Ta oxide film because oxygen may penetrate into the exposed TaN film. As a result, this may adversely affect a work function of a gate stack structure intended to be formed. In addition, PDMAT is a solid at room temperature, and handling of PDMAT may not be facilitated in a process of forming a thin film using ALD or CVD. Thus, PDMAT has a disadvantage in terms of productivity.

According to an embodiment, the thin film forming raw material, which includes the tantalum compound represented by General Formula (I), may be used to form the second etch stop layer 526B, and the second etch stop layer 526B may have excellent etch resistance to $H_2O_2$, even when exposed to $H_2O_2$ included in the etch solution while the first work function adjusting layer 528 is removed. Therefore, there is no concern that the second etch stop layer 526B would be damaged or suffer from a change of composition, and there is no adverse effect in realizing a desired work function of a gate intended to be formed.

Figure 5F:
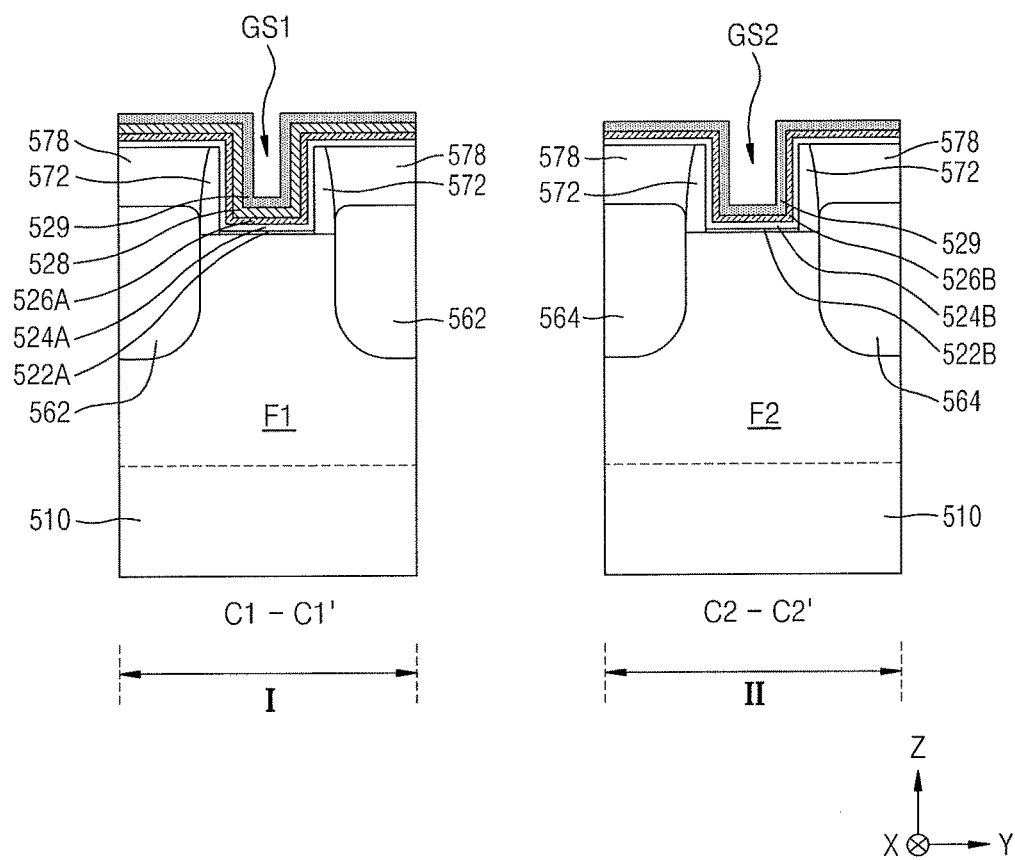

Referring to FIG. 5F, the mask pattern 592 (see FIG. 5E) may be removed, followed by forming the second work function adjusting layer 529, which covers the first work function adjusting layer 528 in the first region I and covers the second etch stop layer 526B in the second region II.

The second work function adjusting layer 529 may include, e.g., TiAl, TiAlC, TiAlN, TaC, TiC, HfSi, or combinations thereof.

Figure 5G:
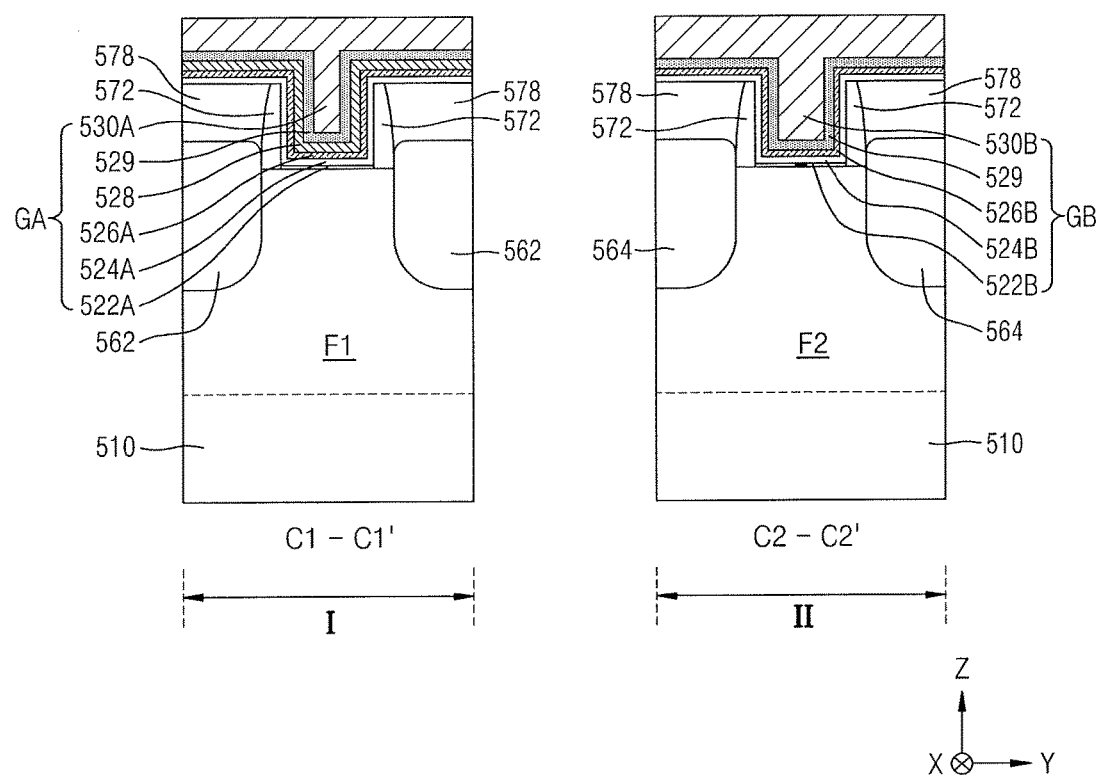

Referring to FIG. 5G, the first gap-fill gate film 530A, which fills the remaining portion of the first gate space GS1 over the second work function adjusting layer 529 in the first region I, may be formed, and the second gap-fill gate film 530B, which fills the remaining portion of the second gate space GS2 over the second work function adjusting layer 529 in the second region II, may be formed.

The first gap-fill gate film 530A and/or the second gap-fill gate film 530B may include, e.g., W. In an implementation, the first gap-fill gate film 530A and the second gap-fill gate film 530B may be simultaneously formed.

In an implementation, the method of fabricating the integrated circuit device 500 may further include a process of forming a conductive barrier film between the second work function adjusting layer 529 in the first region I and the first gap-fill gate film 530A, and/or between the second work function adjusting layer 529 in the second region II and the second gap-fill gate film 530B, before the first gap-fill gate film 530A and the second gap-fill gate film 530B are formed. In an implementation, the conductive barrier film may include a metal nitride, e.g., TiN, TaN, or combinations thereof.

Figure 5H:
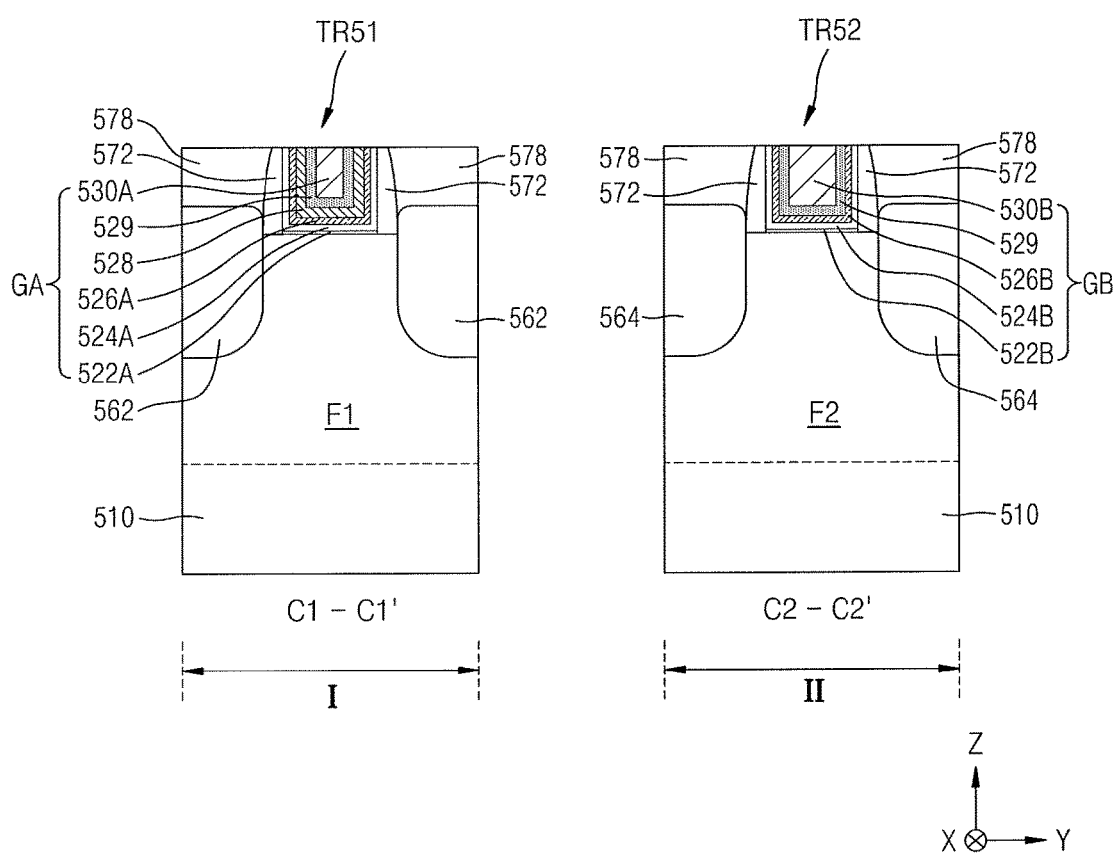

Referring to FIG. 5H, in the first region I and the second region II, the layers covering an upper surface of the insulating film 578 may be removed until the upper surface of the insulating film 578 is exposed, whereby the first and second gate structures GA and GB are respectively formed within the first and second gate spaces GS1 and GS2, and the first transistor TR51 and the second transistor TR52 are completed.

In an implementation, the method of fabricating the integrated circuit device may include a FinFET including a 3-dimensional structured channel. In an implementation, integrated circuit devices including a planar MOSFET having features according to an embodiment may be formed.

FIGS. 6A to 6J illustrate cross-sectional views of stages in a method of fabricating an integrated circuit device 600 (see FIG. 6J) according to embodiments. In FIGS. 6A to 6J, the same reference numerals as in FIGS. 5A to 5H denote the same members, and details thereof may be omitted.

Figure 6A:
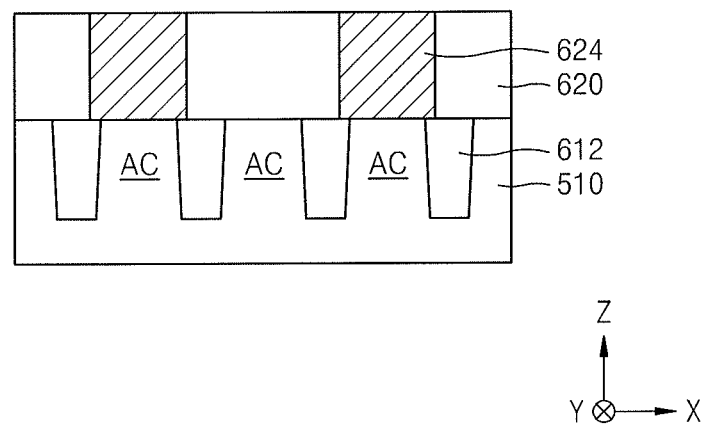
FIGS. 6A to 6J illustrate cross-sectional views of stages in a method of fabricating an integrated circuit device according to embodiments.

Referring to FIG. 6A, an interlayer dielectric 620 may be formed on the substrate 510 including a plurality of active regions AC, followed by forming a plurality of conductive regions 624, which penetrate the interlayer dielectric 620 and are respectively connected to the plurality of active regions AC.

The plurality of active regions AC may be defined by a plurality of device isolation regions 612 formed on the substrate 510. The device isolation regions 612 may include a silicon oxide film, a silicon nitride film, a silicon oxynitride film, or combinations thereof.

The interlayer dielectric 620 may include a silicon oxide film.

The plurality of conductive regions 624 may be connected to one terminal of a switching device such as a field effect transistor formed on the substrate 510. The plurality of conductive regions 624 may include, e.g., polysilicon, a metal, a conductive metal nitride, a metal silicide, or combinations thereof.

Figure 6B:
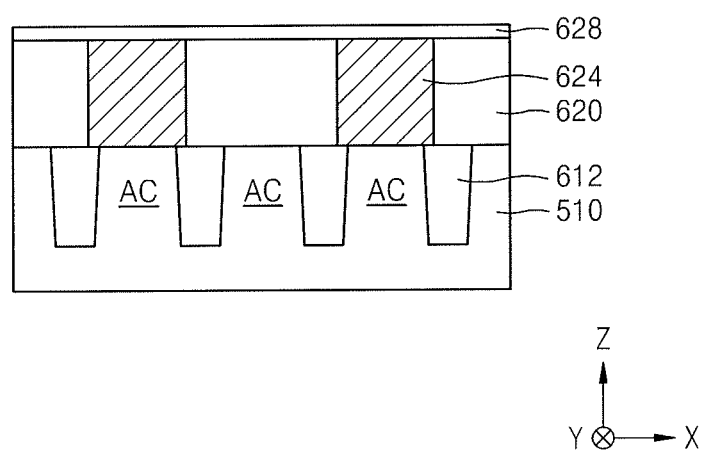

Referring to FIG. 6B, an insulating layer 628 covering the interlayer dielectric 620 and the plurality of conductive regions 624 may be formed. The insulating layer 628 may be used as an etch stop layer.

The insulating layer 628 may include an insulating material having an etch selectivity with respect to the interlayer dielectric 620 and a mold film 630 (see FIG. 6C) which is formed in a subsequent process. In an implementation, the insulating layer 628 may include silicon nitride, silicon oxynitride, or combinations thereof.

In an implementation, the insulating layer 628 may have a thickness of, e.g., about 100 Å to about 600 Å.

Figure 6C:
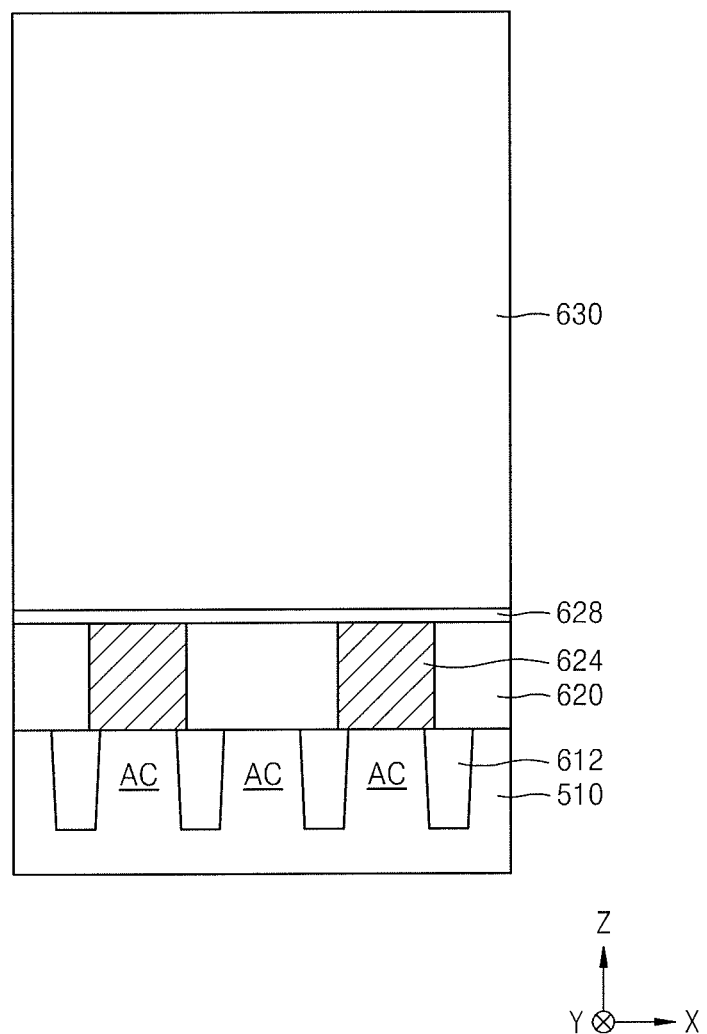

Referring to FIG. 6C, the mold film 630 may be formed on the insulating layer 628.

In an implementation, the mold film 630 may include an oxide film. For example, the mold film 630 may include an oxide film such as borophosphosilicate glass (BPSG), phosphosilicate glass (PSG), undoped silicate glass (USG), spin on dielectric (SOD), an oxide film formed by a high density plasma chemical vapor deposition (HDP CVD) process, or the like. To form the mold film 630, a thermal CVD process or a plasma CVD process may be used. In an implementation, the mold film 630 may have a thickness of, e.g., about 1000 Å to about 20,000 Å.

In an implementation, the mold film 630 may include a support film. The support film may be formed of a material having an etch selectivity with respect to the mold film 630, and may have a thickness of about 50 Å to about 3000 Å. The support film may include a material having a relatively low etch rate with respect to an etch atmosphere, e.g., with respect to a HF/NH$_4$F/H$_2$O etchant (LAL) when the mold film 630 is removed by a LAL lift-off process in a subsequent process. In an implementation, the support film may include, e.g., silicon nitride, silicon carbonitride, tantalum oxide, titanium oxide, or combinations thereof.

Figure 6D:
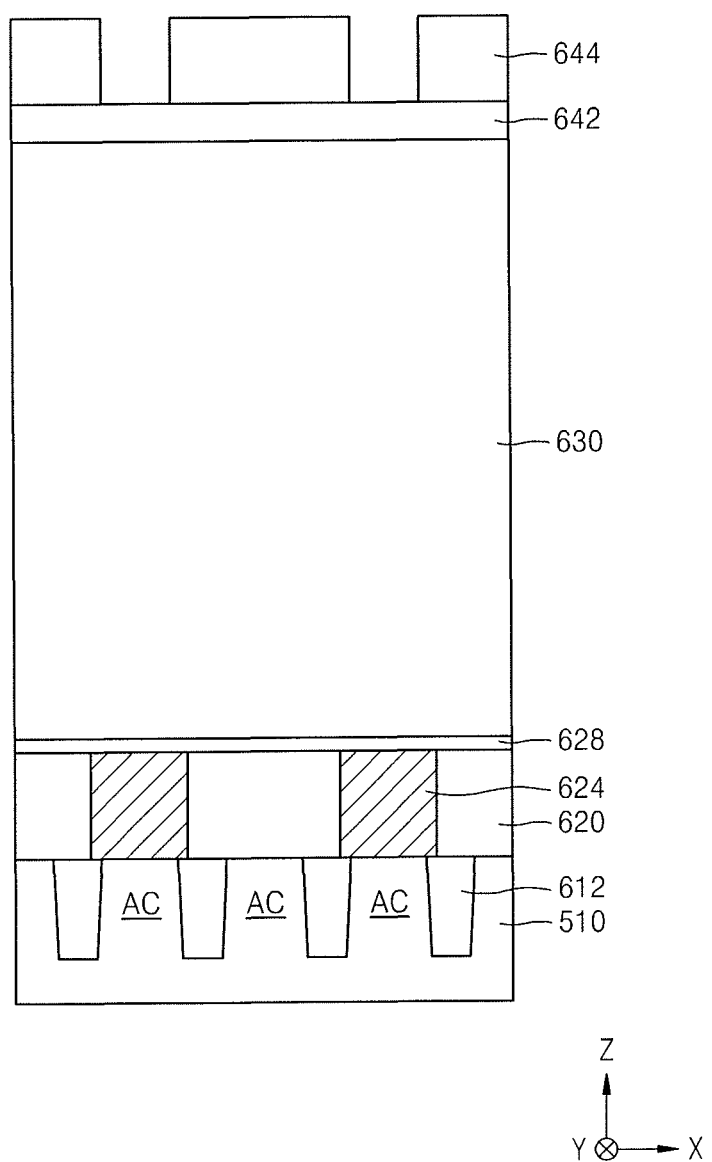

Referring to FIG. 6D, a sacrificial film 642 and a mask pattern 644 may be sequentially formed on the mold film 630.

The sacrificial film 642 may include an oxide film such as BPSG, PSG, USG, SOD, an oxide film formed by a HDP CVD process, or the like. The sacrificial film 642 may have a thickness of about 500 Å to about 2,000 Å. The sacrificial film 642 may protect the support film included in the mold film 630.

The mask pattern 644 may include an oxide film, a nitride film, a polysilicon film, a photoresist film, or combinations thereof. A region in which a lower electrode of a capacitor is formed may be defined by the mask pattern 644.

Figure 6E:
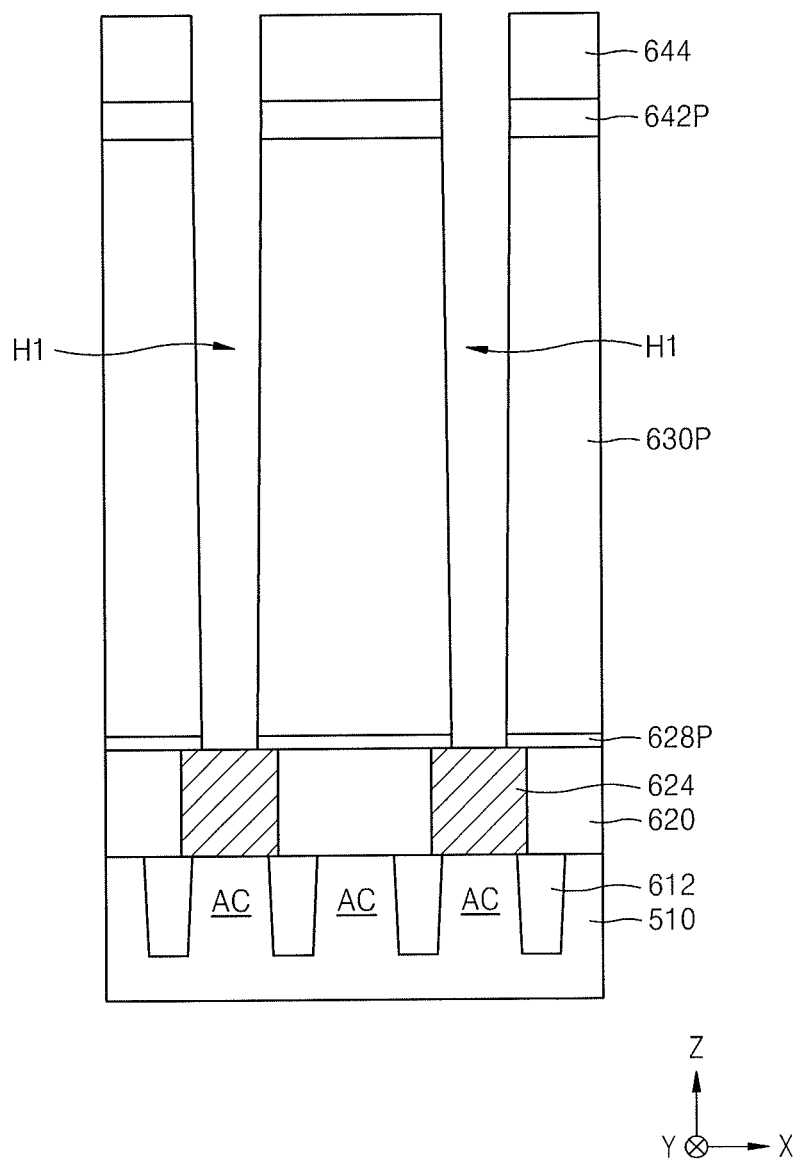

Referring to FIG. 6E, the sacrificial film 642 and the mold film 630 may be dry-etched using the mask pattern 644 as an etch mask and using the insulating layer 628 as an etch stop layer, thereby forming a sacrificial pattern 642P and a mold pattern 630P, which define a plurality of holes H1.

In an implementation, the insulating layer 628 may also be etched due to over-etch, whereby an insulating pattern 628P exposing the plurality of conductive regions 624 may be formed.

Figure 6F:
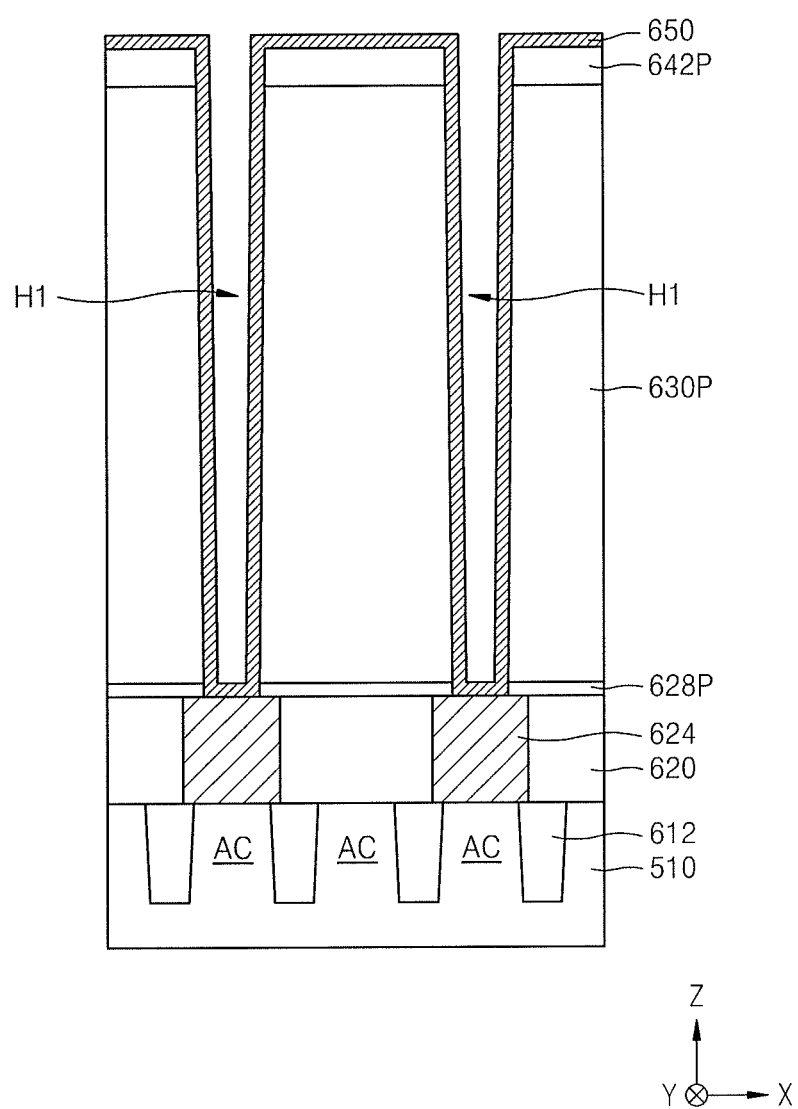

Referring to FIG. 6F, the mask pattern 644 may be removed from the resultant of FIG. 6E, followed by forming a conductive film 650 for forming lower electrodes, which covers an inner sidewall of each of the plurality of holes H1, an exposed surface of the insulating pattern 628P, an exposed surface of each of the plurality of conductive regions 624 inside the plurality of holes H1, and an exposed surface of the sacrificial pattern 642P.

The conductive film 650 for forming lower electrodes may be conformally formed on the sidewalls of the plurality of holes H1 such that an inner space of each of the plurality of holes H1 partially remains.

In an implementation, the conductive film 650 for forming lower electrodes may include a doped semiconductor, a conductive metal nitride, a metal, a metal silicide, a conductive oxide, or combinations thereof. For example, the conductive film 650 for forming lower electrodes may include TiN, TiAlN, TaN, TaAlN, W, WN, Ru, RuO$_2$, SrRuO$_3$, Ir, IrO$_2$, Pt, PtO, SRO (SrRuO$_3$), BSRO ((Ba,Sr)RuO$_3$), CRO (CaRuO$_3$), LSCO ((La,Sr)CoO$_3$), or combinations thereof.

To form the conductive film 650 for forming lower electrodes, a CVD, metal organic CVD (MOCVD), or ALD process may be used. In an implementation, the conductive film 650 for forming lower electrodes may have a thickness of, e.g., about 20 nm to about 100 nm.

Figure 6G:
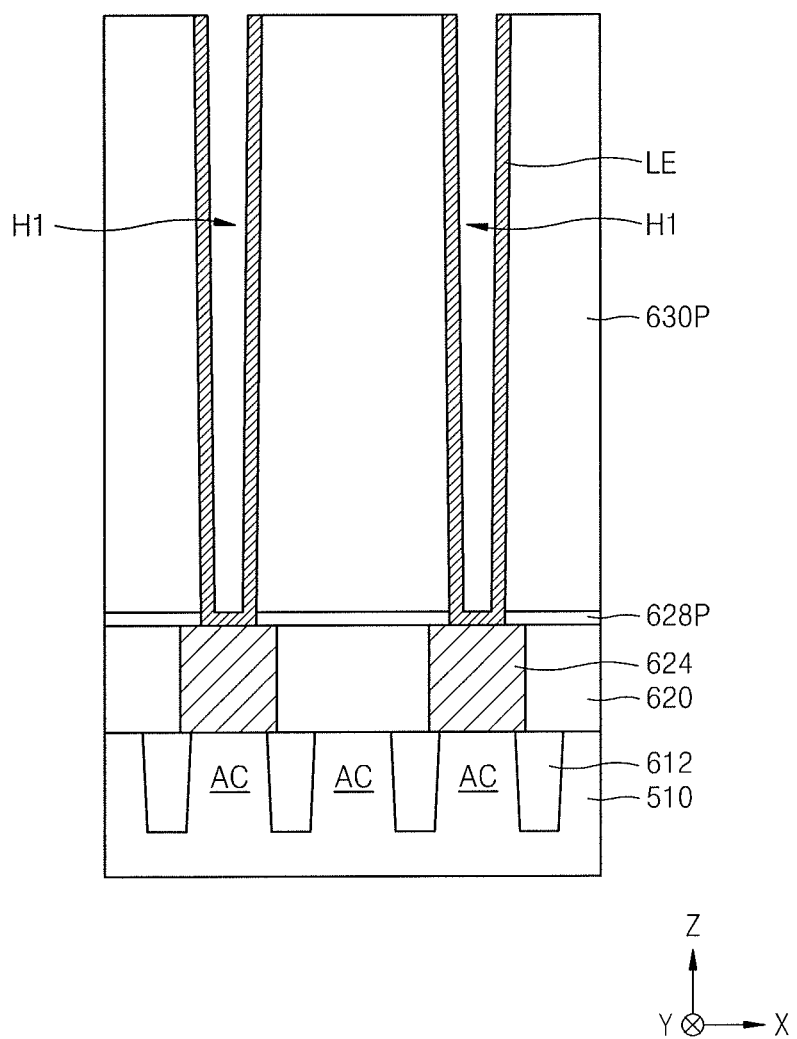

Referring to FIG. 6G, an upper side of the conductive film 650 for forming lower electrodes may be partially removed, thereby dividing the conductive film 650 for forming lower electrodes into a plurality of lower electrodes LE.

To form the plurality of lower electrodes LE, a portion of the upper side of the conductive film 650 for forming lower electrodes and the sacrificial pattern 642P (see FIG. 6F) may be removed by using an etchback or chemical mechanical polishing (CMP) process until an upper surface of the mold pattern 630P is exposed.

The plurality of lower electrodes LE may be connected to the conductive regions 624 through the insulating pattern 628P.

Figure 6H:
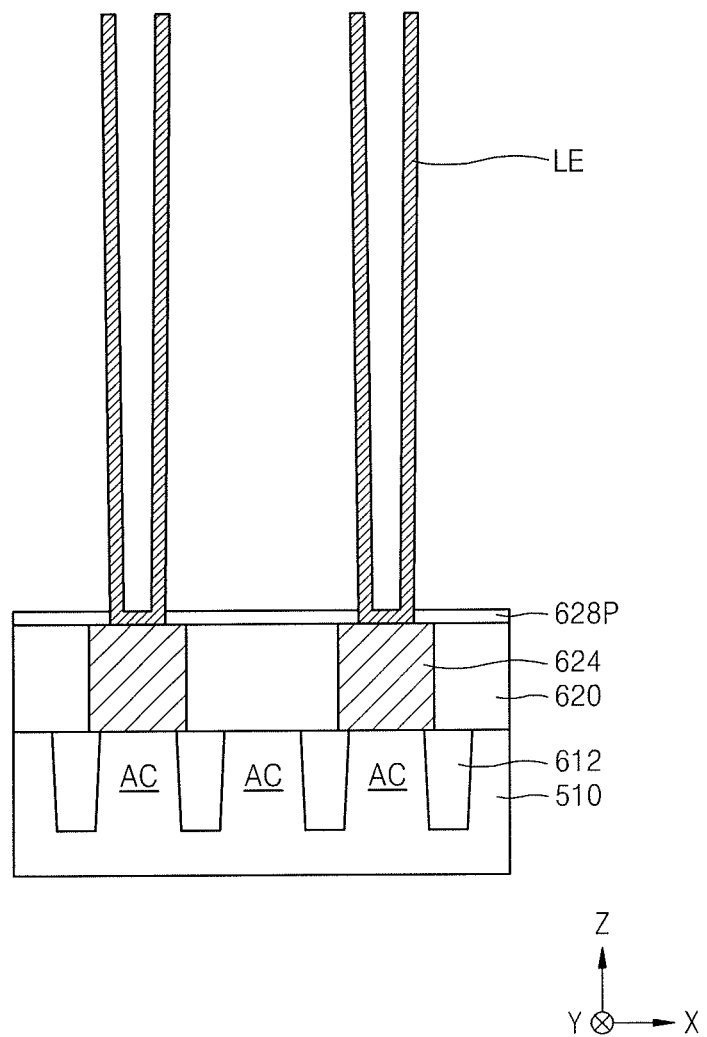

Referring to FIG. 6H, the mold pattern 630P is removed, thereby exposing outer walls of the plurality of lower electrodes LE having cylindrical shapes.

The mold pattern 630P may be removed by a lift-off process using LAL or hydrofluoric acid.

Figure 6I:
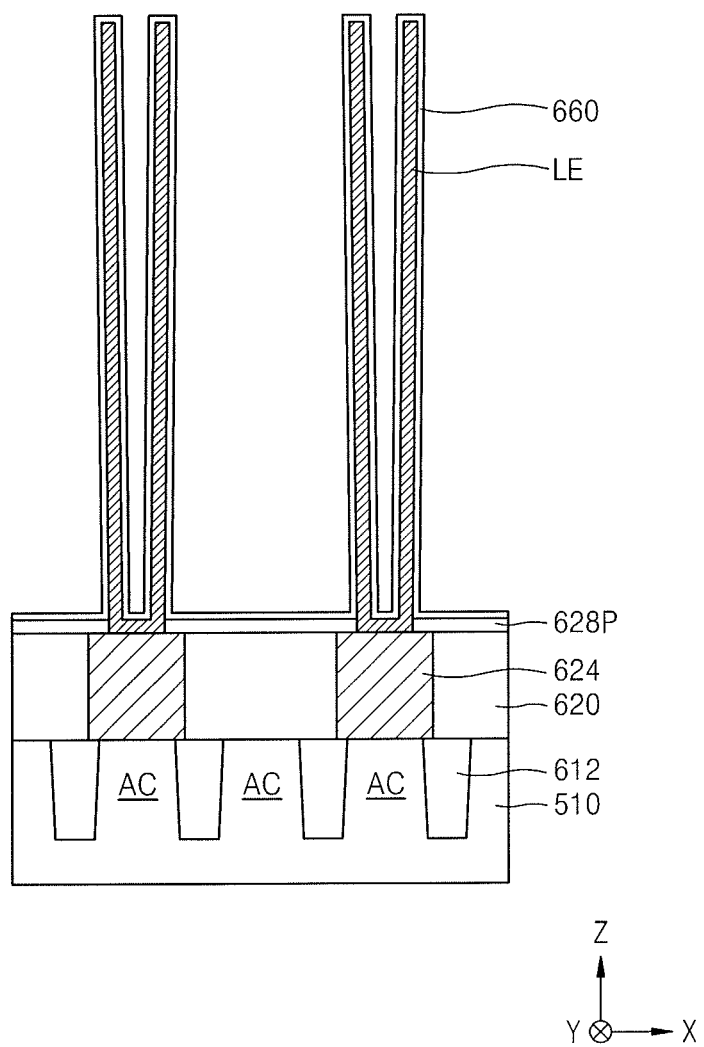

Referring to FIG. 6I, a dielectric film 660 may be formed on the plurality of lower electrodes LE.

The dielectric film 660 may conformally cover exposed surfaces of the plurality of lower electrodes LE.

The dielectric film 660 may be formed by an ALD process. To form the dielectric film 660, the method of forming the thin film, according to an embodiment, which has been described with reference to FIGS. 1 and 3, may be used.

In an implementation, the dielectric film 660 may include, e.g., a Ta$_2$O$_5$ film. For example, the dielectric film 660 may include a single layer of a Ta$_2$O$_5$ film, or may include a multiple layers which includes at least one Ta$_2$O$_5$ film and at least one dielectric film including oxide, a metal oxide, nitride, or combinations thereof. In an implementation, the dielectric film 660 may include a combination of at least one Ta$_2$O$_5$ film and at least one high-K dielectric film selected from a ZrO$_2$ film and an Al$_2$O$_3$ film.

In an implementation, the dielectric film 660 may have a thickness of, e.g., about 50 Å to about 150 Å.

Figure 6J:
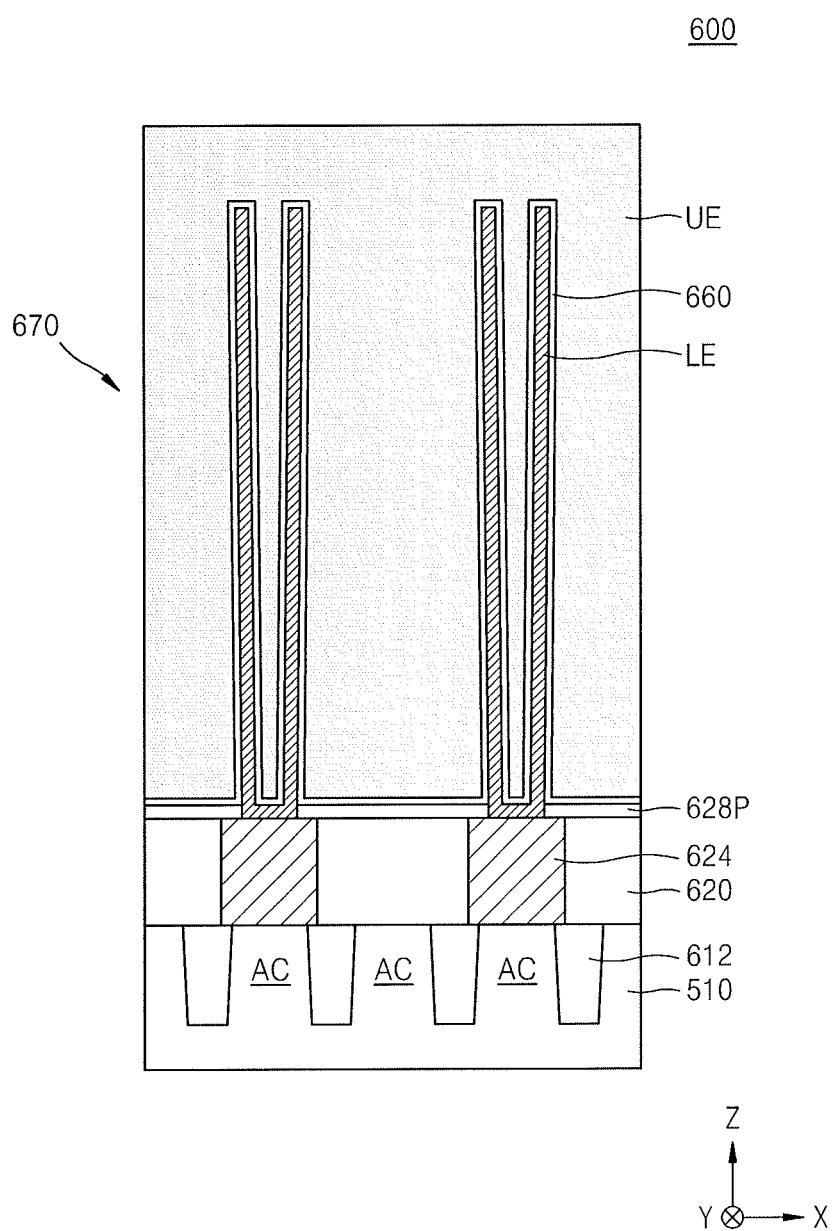

Referring to FIG. 6J, an upper electrode UE may be formed on the dielectric film 660.

The lower electrode LE, the dielectric film 660, and the upper electrode UE may constitute a capacitor 670.

The upper electrode UE may include a doped semiconductor, a conductive metal nitride, a metal, a metal silicide, a conductive oxide, or combinations thereof. In an implementation, the upper electrode UE may include, e.g., TiN, TiAlN, TaN, TaAlN, W, WN, Ru, RuO$_2$, SrRuO$_3$, Ir, IrO$_2$, Pt, PtO, SRO (SrRuO$_3$), BSRO ((Ba,Sr)RuO$_3$), CRO (CaRuO$_3$), LSCO ((La,Sr)CoO$_3$), or combinations thereof.

To form the upper electrode UE, a CVD, MOCVD, PVD, or ALD process may be used.

In an implementation, the method of fabricating the integrated circuit device 600 may include the process of forming the dielectric film 660 covering a surface of the cylindrical lower electrode LE. In an implementation, a pillar-type lower electrode having no inner space may be formed instead of the cylindrical lower electrode LE, and the dielectric film 660 may be formed on the pillar-type lower electrode.

The capacitor 670 of the integrated circuit device 600, which is formed by the method according to embodiments as described with reference to FIGS. 6A to 6J, may include the lower electrode LE having a 3-dimensional electrode structure in order to increase capacitance thereof. To compensate reduction of capacitance due to reduction of a design rule, an aspect ratio of the 3-dimensional structured lower electrode LE may be increasing. To form a high-quality dielectric film in a narrow and deep 3-dimensional space, an ALD or CVD process may be used. The tantalum compound according to an embodiment may have a relatively low melting point, may be delivered in a liquid state, and may be easily vaporized due to the relatively high vapor pressure thereof, delivery of the tantalum compound may be facilitated. Thus, in forming the dielectric film 660 on the lower electrode LE by using the ALD or CVD process, the raw material compound including the tantalum compound for forming the dielectric film 660 may be easily delivered to a structure having a relatively high aspect ratio. Therefore, the dielectric film 660 exhibiting good step coverage may be formed on the lower electrode LE having a relatively high aspect ratio.

Figure 7:
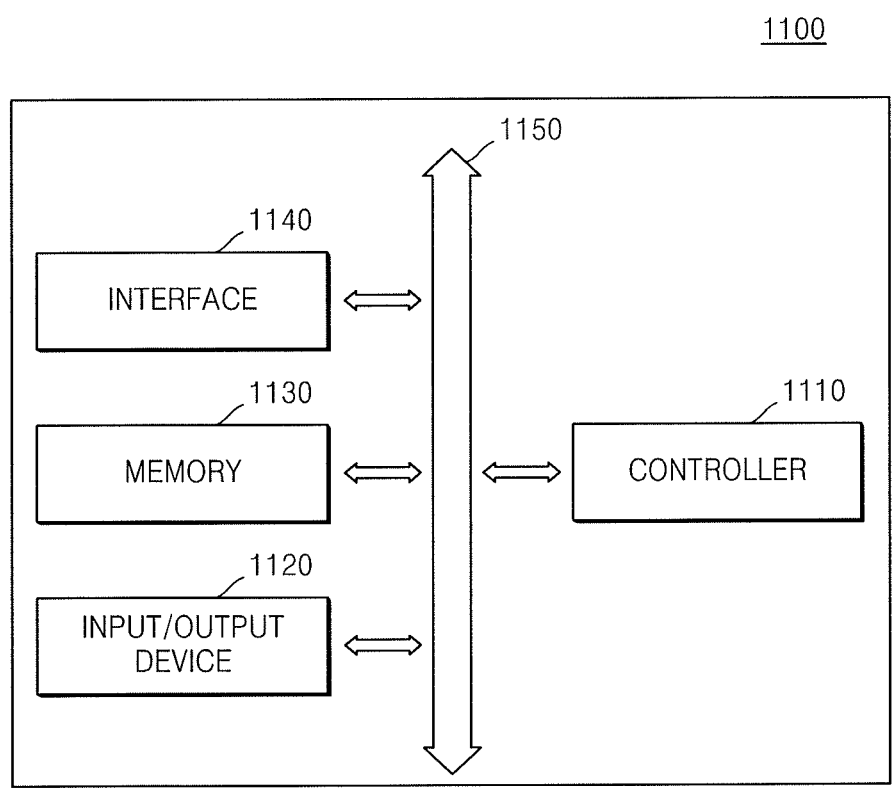
FIG. 7 illustrates a schematic block diagram showing main components of an electronic device according to embodiments.

FIG. 7 illustrates a block diagram showing main components of an electronic device according to embodiments.

An electronic device 1100 may include a controller 1110, an input/output device 1120, a memory 1130, and an interface 1140. The electronic device 1100 may be a mobile system, or a system transmitting or receiving information. In some embodiments, the mobile system may include at least one of a personal digital assistant (PDA), a portable computer, a web tablet, a wireless phone, a mobile phone, a digital music player, and a memory card.

In an implementation, the controller 1110 may be a microprocessor, a digital signal processor, or a micro-controller.

The input/output device 1120 may be used for data input and output of the electronic device 1100. The electronic device 1100 may be connected to devices external to the electronic device 1100, for example, a personal computer or a network by using the input/output device 1120, and may exchange data with the external devices. In an implementation, the input/output device 1120 is a keypad, a keyboard, or a display.

In an implementation, the memory 1130 stores codes and/or data for operations of the controller 1110. In some other embodiments, the memory 1130 stores data processed by the controller 1110. At least one of the controller 1110 and the memory 1130 includes the tantalum-containing film formed by the method of forming the thin film, according to the inventive concept, the integrated circuit device 500 formed by the method described with reference to FIGS. 5A to 5H, or the integrated circuit device 600 formed by the method described with reference to FIGS. 6A to 6J.

The interface 1140 may serve as a data transmitting path between the electronic device 1100 and other devices external to the electronic device 1100. The controller 1110, the input/output device 1120, the memory 1130, and the interface 1140 may communicate with each other through a bus 1150.

The electronic device 1100 may be included in mobile phones, MP3 players, navigation systems, portable multimedia players (PMPs), solid state disks (SSDs), or household appliances.

Hereinafter, the tantalum compound and the method of forming the thin film will be explained in more detail with reference to some examples.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Example 1

Synthesis of Tantalum Compound Represented by Formula 12

20.0 g (55.8 mmol) of tantalum (V) chloride, 15.2 g (112 mmol) of zinc chloride, and 154 g of toluene were added into a 500 mL 4-neck flask. 5.03 g (55.8 mmol) of ethylene glycol dimethyl ether was added dropwise into the flask, followed by stirring the components for 1 hour. 9.90 g (167 mmol) of isopropylamine was added dropwise to the reaction liquid while the reaction liquid was cooled to 0° C. After completion of the dropwise addition, the reaction liquid was heated to 25° C., followed by stirring the reaction liquid at 25° C. for 12 hours. After completion of the stirring, the reaction liquid was filtered, thereby obtaining a liquid. The solvent was removed from the obtained liquid, followed by adding 150 g of toluene to the resultant, thereby obtaining a solution A.

10.3 g (102 mmol) of diisopropylamine and 87 g of toluene were added into a separate 300 mL 4-neck flask, followed by adding 64.2 mL of a solution of n-butyl lithium in n-hexane (n-butyl lithium amount: 98.9 mmol) dropwise into the flask while the flask was cooled to 0° C. After completion of the dropwise addition, the components were stirred at 25° C. for 4 hours, thereby preparing a lithium diisopropylamide solution A.

The lithium diisopropylamide solution A was added dropwise to the solution A while the solution A was cooled to 0° C. After completion of the dropwise addition, the components were stirred at 25° C. for 12 hours, and then stirred under reflux for 6 hours. The reaction liquid was filtered, followed by adding 13.5 mL of a solution of methyl lithium in diethyl ether (methyl lithium amount: 15.6 mmol) to the reaction liquid, and then stirred at 25° C. for 4 hours. The reaction liquid was filtered, followed by removing the solvent from the reaction liquid. Next, the resultant was distilled at a bath temperature of 115° C. at 50 Pa, thereby obtaining 5.04 g of a pale yellow transparent liquid (yield: 19.9%).

(Analysis)

(1) Thermogravimetry-Differential Thermal Analysis (TG-DTA) Under Atmospheric Pressure 50% mass reduction temperature: 175° C. (Ar flow rate: 100 mL/min, heating rate: 10° C./min, sample amount: 4.070 mg)

(2) TG-DTA Under Reduced Pressure

50% mass reduction temperature: 118° C. (10 Torr, Ar flow rate: 50 mL/min, heating rate: 10° C./min, sample amount: 10.708 mg)

(3) $^1$H-NMR (Solvent: hexadeuterobenzene) (Chemical Shift:Multiplicity:Number of H)

(4.65:Sep:1H) (3.57:Sep:4H) (1.48:d:6H) (1.27:d:12H) (1.19:d:12H) (0.45:s:3H)

(4) Elemental Analysis

Amount of tantalum (ICP-AES): 40.8% (theoretical value: 39.9%)

Amounts of C, H, and N: C 41.4% (theoretical value: 42.4%), H 7.5% (theoretical value: 8.5%), N 8.2% (theoretical value: 9.3%)

(5) ASAP-TOF MS: m/z 454.2624 (Theoretical Value: 454.2624 [M+H])

Figure 8:
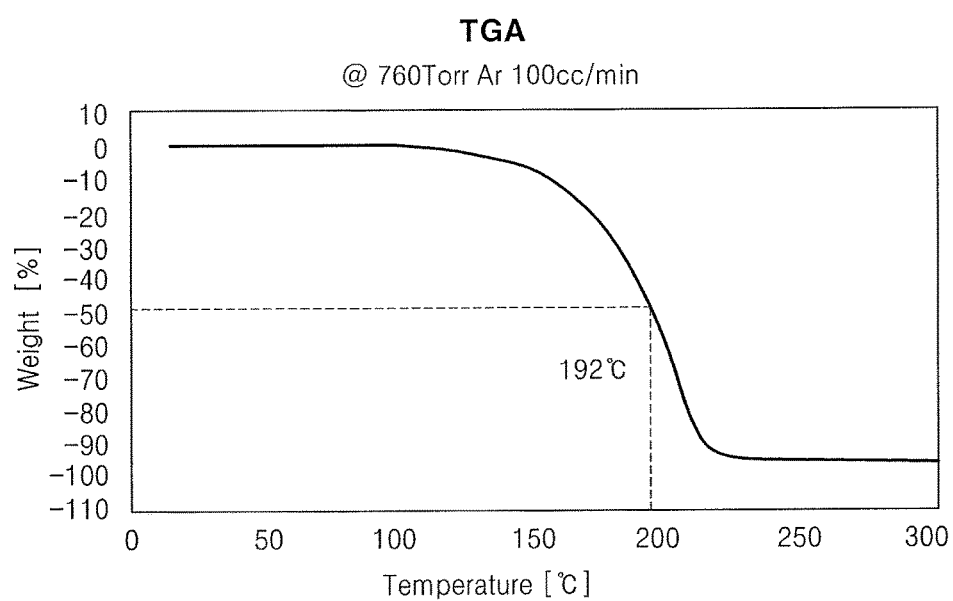
FIG. 8 illustrates a graph showing results of thermal gravimetric analysis (TGA) of a tantalum compound according to an embodiment.

FIG. 8 illustrates a graph showing results of thermal gravimetric analysis (TGA) of the tantalum compound represented by Formula 12, the tantalum compound being synthesized in Example 1.

For the evaluation of FIG. 8, the TGA was performed under an Ar flowing atmosphere. When 10 mg of the tantalum compound synthesized in Example 1 was heated at a heating rate of 10° C./min, the mass of the tantalum compound was reduced by 50% at 192° C.

Figure 9:
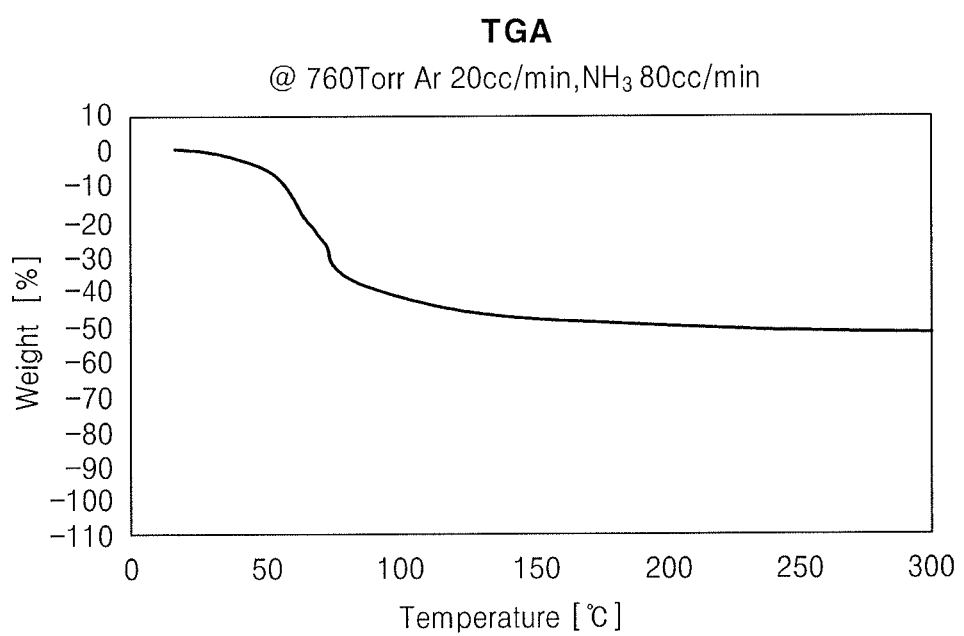
FIG. 9 illustrates a graph showing other results of TGA of a tantalum compound according to an embodiment.

FIG. 9 illustrates a graph showing other results of TGA of the tantalum compound represented by Formula 12, the tantalum compound being synthesized in Example 1.

In the evaluation of FIG. 9, the TGA was performed under an atmosphere of an ammonia reducing gas in order to confirm reactivity of the tantalum compound with ammonia. When 10 mg of the tantalum compound synthesized in Example 1 was heated at a heating rate of 10° C./min, it was confirmed that the tantalum compound started to show reduction of mass at about 50° C. and reacted with ammonia.

Figure 10:
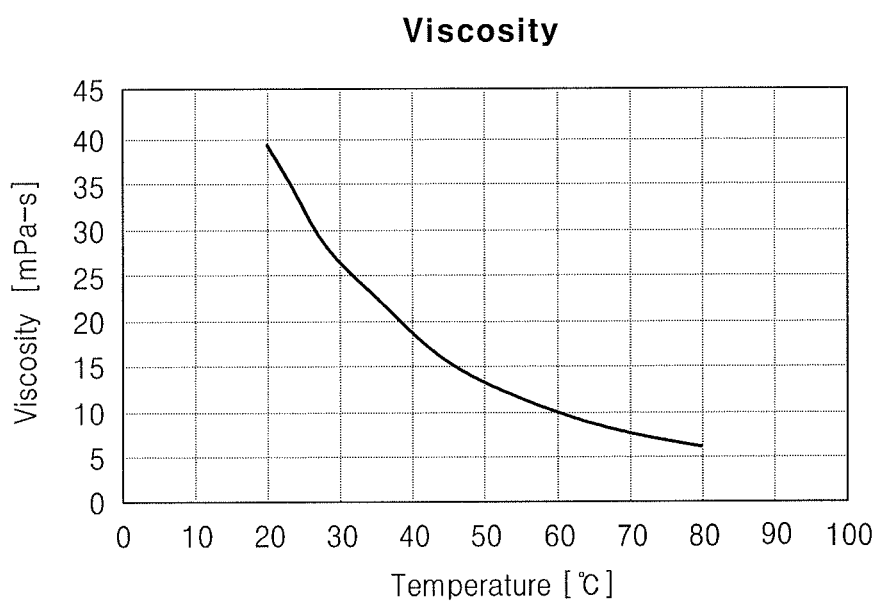
FIG. 10 illustrates a graph showing measurement results of viscosity along with temperature for a tantalum compound according to an embodiment.

FIG. 10 illustrates a graph showing measurement results of viscosity along with temperature for the tantalum compound represented by Formula 12, the tantalum compound being synthesized in Example 1.

As a result of the evaluation of FIG. 10, it may be seen that the viscosity of the tantalum compound represented by Formula 12 was 31.9 mPa·s at room temperature (~25° C.).

Example 2

Synthesis of Tantalum Compound Represented by Formula 18

10.0 g (27.9 mmol) of tantalum (V) chloride, 7.61 g (55.8 mmol) of zinc chloride, and 77.0 g of toluene were added into a 300 mL 4-neck flask. 2.52 g (27.9 mmol) of ethylene glycol dimethyl ether was added dropwise into the flask, followed by stirring the components for 1 hour. 6.13 g (83.8 mmol) of t-butylamine was added dropwise to the reaction liquid while the reaction liquid was cooled to 0° C. After completion of the dropwise addition, the reaction liquid was heated to 25° C., followed by stirring the reaction liquid at 25° C. for 12 hours. After completion of the stirring, the reaction liquid was filtered, thereby obtaining a liquid. The solvent was removed from the obtained liquid, followed by adding 75 g of toluene to the resultant, thereby obtaining a solution B.

5.2 g (51.4 mmol) of diisopropylamine and 44 g of toluene were added into a separate 200 mL 4-neck flask, followed by adding 32.1 mL of a solution of n-butyl lithium in n-hexane (n-butyl lithium amount: 49.4 mmol) dropwise into the flask while the flask was cooled to 0° C. After completion of the dropwise addition, the components were stirred at 25° C. for 4 hours, thereby preparing a lithium diisopropylamide solution B.

The lithium diisopropylamide solution B was added dropwise to the solution B while the solution B was cooled to 0° C. After completion of the dropwise addition, the components were stirred at 25° C. for 12 hours, and then stirred under reflux for 6 hours. The reaction liquid was filtered, followed by adding 4.7 mL of a solution of methyl lithium in diethyl ether (methyl lithium amount: 5.5 mmol) to the reaction liquid, and then stirred at 25° C. for 4 hours. The reaction liquid was filtered, followed by removing the solvent from the reaction liquid. Next, the resultant was distilled at a bath temperature of 135° C. at 50 Pa, thereby obtaining 1.55 g of a pale yellow transparent liquid (yield: 11.9%).

(Analysis)

(1) TG-DTA Under Atmospheric Pressure

50% mass reduction temperature: 200° C. (Ar flow rate: 100 mL/min, heating rate: 10° C./min, sample amount: 10.113 mg)

(2) TG-DTA Under Reduced Pressure

50% mass reduction temperature: 122° C. (10 Torr, Ar flow rate: 50 mL/min, heating rate: 10° C./min, sample amount: 10.063 mg)

(3) $^1$H-NMR (Solvent: hexadeuterobenzene) (Chemical Shift:Multiplicity:Number of H)

(3.57:Sep:4H) (1.61:s:9H) (1.27:d:12H) (1.20:d:12H) (0.45:s:3H)

(4) Elemental Analysis

Amount of tantalum (ICP-AES): 39.5% (Theoretical Value: 38.7%)

Amounts of C, H, and N: C 41.4% (theoretical value: 43.7%), H 7.5% (theoretical value: 8.6%), N 8.1% (theoretical value: 9.0%)

(5) ASAP-TOF MS: m/z 468.2782 (Theoretical Value: 468.2780 [M+H])

Example 3

Synthesis of Tantalum Compound Represented by Formula 48

20.0 g (55.8 mmol) of tantalum (V) chloride, 15.2 g (112 mmol) of zinc chloride, and 154 g of toluene were added into a 500 mL 4-neck flask. 5.03 g (55.8 mmol) of ethylene glycol dimethyl ether was added dropwise into the flask at ambient temperature, followed by stirring the components for 1 hour. 9.90 g (167 mmol) of isopropylamine was added dropwise to the reaction liquid while the reaction liquid was cooled to 0° C. After completion of the dropwise addition, the reaction liquid was heated to 25° C., followed by stirring the reaction liquid at 25° C. for 12 hours. After completion of the stirring, the reaction liquid was filtered, thereby obtaining a liquid. The solvent was removed from the obtained liquid, followed by adding 150 g of toluene to the resultant, thereby obtaining a solution C.

10.3 g (102 mmol) of diisopropylamine and 87 g of toluene were added into a separate 300 mL 4-neck flask, followed by adding 64.2 mL of a solution of n-butyl lithium in n-hexane (n-butyl lithium amount: 98.9 mmol) dropwise into the flask while the flask was cooled to 0° C. After completion of the dropwise addition, the components were stirred at 25° C. for 4 hours, thereby preparing a lithium diisopropylamide solution C.

The lithium diisopropylamide solution C was added dropwise to the solution C while the solution C was cooled to 0° C. After completion of the dropwise addition, the components were stirred at 25° C. for 12 hours, and then stirred under reflux for 6 hours. The reaction liquid was filtered, followed by adding 21.7 mL of a solution of isopropylmagnesium bromide in tetrahydrofuran (isopropylmagnesium bromide amount: 15.6 mmol) to the reaction liquid, and then stirred at 25° C. for 4 hours. The reaction liquid was filtered, followed by removing the solvent from the reaction liquid. Next, the resultant was distilled at a bath temperature of 140° C. at 50 Pa, thereby obtaining 3.40 g of a pale yellow transparent liquid (yield: 12.6%).

(Analysis)

(1) TG-DTA Under Atmospheric Pressure

50% mass reduction temperature: 213° C. (Ar flow rate: 100 mL/min, heating rate: 10° C./min, sample amount: 9.850 mg)

(2) TG-DTA Under Reduced Pressure

50% mass reduction temperature: 130° C. (10 Torr, Ar flow rate: 50 mL/min, heating rate: 10° C./min, sample amount: 9.775 mg)

(3) $^1$H-NMR (Solvent: hexadeuterobenzene) (Chemical Shift:Multiplicity:Number of H)

(4.65:Sep:1H) (3.59:Sep:4H) (1.83:d:6H) (1.48:d:6H) (1.30:d:12H) (1.19:d:12H) (1.16:Sep:1H)

(4) Elemental Analysis

Amount of tantalum (ICP-AES): 38.2% (theoretical value: 37.6%)

Amounts of C, H, and N: C 42.7% (theoretical value: 44.9%), H 8.0% (theoretical value: 8.8%), N 7.5% (theoretical value: 8.7%)

(5) ASAP-TOF MS: m/z 482.2940 (Theoretical Value: 482.2937 [M+H])

Example 4

Formation of Tantalum Nitride Film

Using each of the tantalum compounds represented by Formulae 12, 18, and 48 as a raw material and using the deposition apparatus shown in FIG. 2A, a tantalum nitride film was formed on a silicon substrate by an ALD process. Conditions of the ALD process for forming the tantalum nitride film were as follows.

(Conditions)

Reaction temperature (substrate temperature): 200° C.

Reactive gas: NH$_3$ 100%

(Process)

Under the above conditions, when the following series of processes (1) to (4) was defined as 1 cycle, 250 cycles were repeated.

Process (1): A process of performing deposition at a pressure of 100 Pa for 10 seconds by introducing vapor of the raw material for CVD into the reaction chamber, the vapor being obtained by vaporizing the raw material under the conditions of a raw material container heating temperature of 70° C. and a raw material container pressure of 100 Pa.

Process (2): A process of removing the unreacted raw material by performing Ar purge for 10 seconds.

Process (3): A process of performing reaction at a pressure of 100 Pa for 60 seconds by introducing the reactive gas into the reaction chamber.

Process (4): A process of removing the unreacted raw material by performing Ar purge for 10 seconds.

Film thickness measurement by X-ray reflectivity, and analysis of structure and composition of the thin film by X-ray diffraction and X-ray photoelectron spectroscopy, were performed on each tantalum nitride film obtained by performing processes set forth above. As a result, all of the obtained thin films had a thickness of 10 nm to 15 nm, and all of the thin films had a composition of tantalum nitride. Carbon content in each of the thin films was less than about 3.0 atom %. In addition, the thickness of the film obtained for every 1 cycle of the ALD process ranged from about 0.04 nm to about 0.06 nm.

Figure 11:
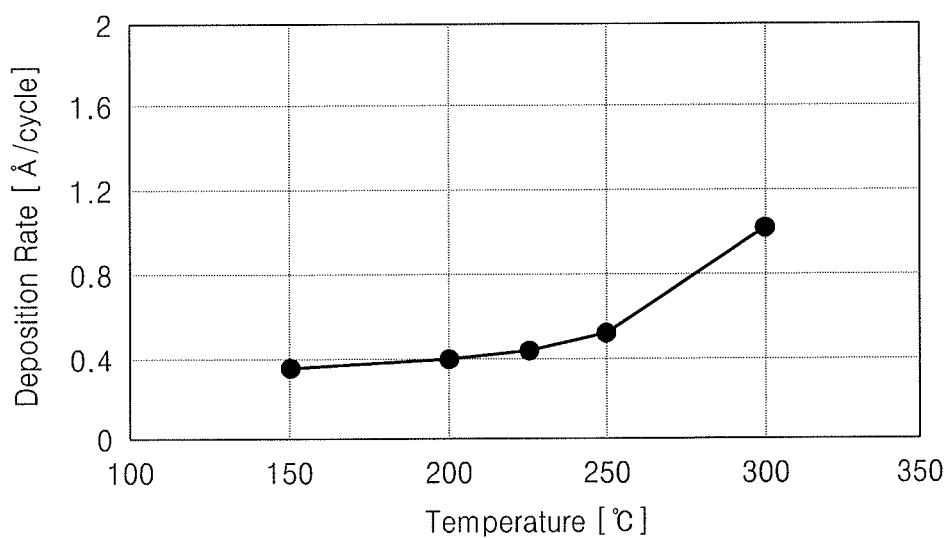
FIG. 11 illustrates a graph showing measurement results of deposition rate along with deposition temperature for a tantalum nitride film formed by using a tantalum compound according to an embodiment.

FIG. 11 illustrates a graph showing measurement results of deposition rate along with deposition temperature for the tantalum nitride film obtained in Example 4 by using the tantalum compound represented Formula 12.

As a result of the evaluation of FIG. 11, it was confirmed that the tantalum nitride film showed ALD behaviors in which a deposition rate was constant in a specific temperature range.

Figure 12:
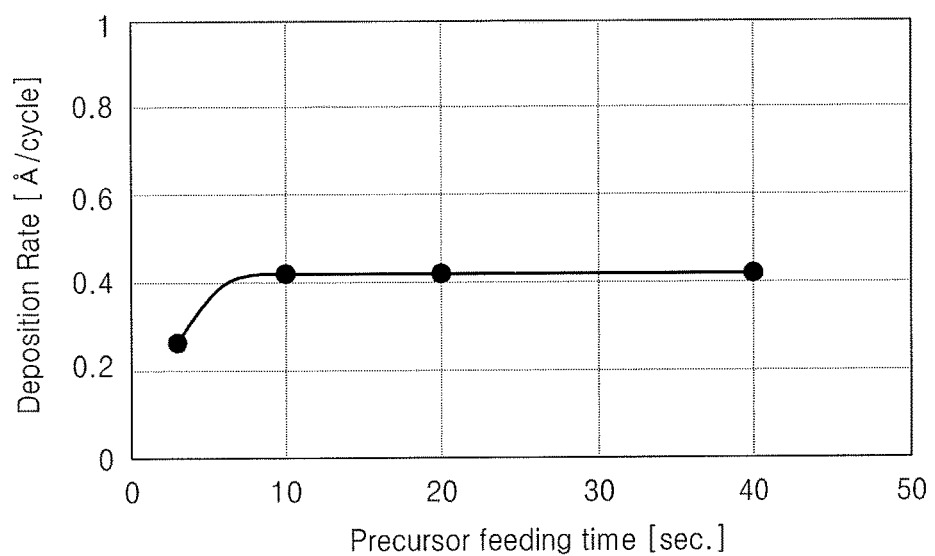
FIG. 12 illustrates a graph showing measurement results of deposition rate along with precursor supply time for a tantalum nitride film formed by using a tantalum compound according to an embodiment.

FIG. 12 illustrates a graph showing measurement results of deposition rate along with precursor supply time for the tantalum nitride film obtained in Example 4 by using the tantalum compound represented Formula 12.

For the evaluation of FIG. 12, using the tantalum compound, which is represented by Formula 2 and was synthesized in Example 1, as a tantalum precursor supplied into a reaction chamber, the deposition rate along with time for supplying the precursor into the reaction chamber was evaluated. As a result, it was confirmed that since the tantalum compound represented by Formula 12 and synthesized in Example 1 showed ideal ALD behaviors, the equal deposition rate was obtained even though the precursor supply time was changed.

Figure 13:
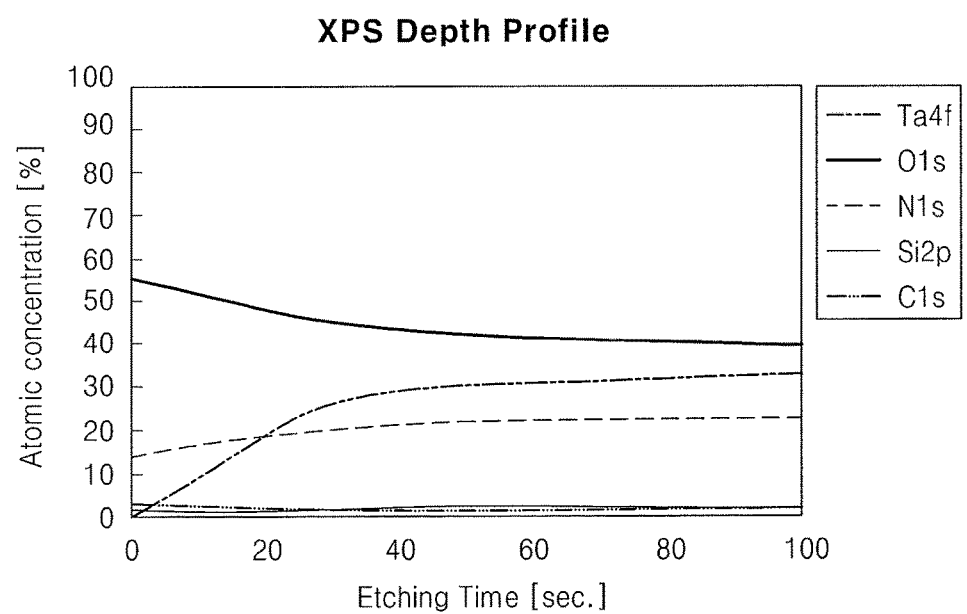
FIG. 13 illustrates a graph showing X-ray photoelectron spectroscopy (XPS) depth profiling results for analyzing concentrations of components of a tantalum nitride film formed by using a tantalum compound according to an embodiment.

FIG. 13 illustrates a graph showing X-ray photoelectron spectroscopy (XPS) depth profiling results for analyzing concentrations of components of the tantalum nitride film obtained in Example 4 by using the tantalum compound represented Formula 12.

It was confirmed that the amount of carbon atoms detected in the tantalum nitride film obtained by using the tantalum compound represented Formula 12 was less than about 3 atom %, and impurities due to decomposition of the precursor were not generated.

Comparative Example 1

Using the following Comparative compound 1 as a raw material for CVD and using the deposition apparatus shown in FIG. 2A, a tantalum nitride film was formed on a silicon substrate by an ALD process.

Comparative compound 1

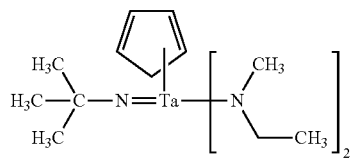

(Conditions)
Reaction temperature (substrate temperature): 200° C.
Reactive gas: NH$_3$ 100%
(Process)
Under the above conditions, when the following series of processes (1) to (4) was defined as 1 cycle, 250 cycles were repeated.

Process (1): A process of performing deposition at a pressure of 100 Pa for 10 seconds by introducing vapor of the raw material for CVD into the reaction chamber, the vapor being obtained by vaporizing the raw material under the conditions of a raw material container heating temperature of 80° C. and a raw material container pressure of 100 Pa.

Process (2): A process of removing the unreacted raw material by performing Ar purge for 10 seconds.

Process (3): A process of performing reaction at a pressure of 100 Pa for 60 seconds by introducing the reactive gas into the reaction chamber.

Process (4): A process of removing the unreacted raw material by performing Ar purge for 10 seconds.

Film thickness measurement by X-ray reflectivity, and analysis of structure and composition of the thin film by X-ray diffraction and X-ray photoelectron spectroscopy were performed on the obtained thin film. As a result, the obtained thin film had a thickness of 5 nm, and had a composition of tantalum nitride. Carbon content in the thin film was 25.0 atom %. In addition, the thickness of the film obtained for every 1 cycle of the ALD process was about 0.02 nm.

From the results of Example 4 and Comparative Example 1, it may be seen that when the tantalum compound according to an embodiment was used as the raw material for the ALD process, the good-quality tantalum nitride thin film could be formed due to the low amount of carbon in the film.

Example 5

Formation of Tantalum Oxide Film

Using each of the tantalum compounds represented by Formulae 12, 18, and 48 as a raw material and using the deposition apparatus shown in FIG. 2A, a tantalum oxide film was formed on a silicon substrate by an ALD process. Conditions of the ALD process for forming the tantalum oxide film were as follows.
(Conditions)
Reaction temperature (substrate temperature): 200° C.
Reactive gas: Ozone 20 mass %+Oxygen 80 mass %
(Process)
Under the above conditions, when the following series of processes (1) to (4) was defined as 1 cycle, 250 cycles were repeated.

Process (1): A process of performing deposition at a pressure of 100 Pa for 10 seconds by introducing vapor of the raw material for CVD into the reaction chamber, the vapor being obtained by vaporizing the raw material under the conditions of a raw material container heating temperature of 70° C. and a raw material container pressure of 100 Pa.

Process (2): A process of removing the unreacted raw material by performing Ar purge for 10 seconds.

Process (3): A process of performing reaction at a pressure of 100 Pa for 10 seconds by introducing the reactive gas into the reaction chamber.

Process (4): A process of removing the unreacted raw material by performing Ar purge for 10 seconds.

Film thickness measurement by X-ray reflectivity, and analysis of structure and composition of the thin film by X-ray diffraction and X-ray photoelectron spectroscopy were performed on each of the tantalum oxide films obtained by performing processes set forth above. As a result, all of the obtained thin films had a thickness of 20 nm to 30 nm, and all of the thin films had a composition of tantalum oxide. Carbon content in each of the thin films was less than about 0.5 atom %. In addition, the thickness of the film obtained for every 1 cycle of the ALD process ranged from about 0.08 nm to about 0.12 nm.

From the results of Example 5, it may be seen that when the tantalum compound according to an embodiment was used as the raw material for the ALD process, a good-quality tantalum oxide thin film was formed, e.g., due to the low amount of carbon in the film.

Example 6

Formation of Metallic Tantalum Film

Using each of the tantalum compounds represented by Formulae 12, 18, and 48 as a raw material and using the deposition apparatus shown in FIG. 2A, a metallic tantalum thin film was formed on a silicon substrate by an ALD process. Conditions of the ALD process for forming the metallic tantalum film were as follows.
(Conditions)
Reaction temperature (substrate temperature): 250° C.
Reactive gas: Hydrogen gas 100%
(Process)
Under the above conditions, when the following series of processes (1) to (4) was defined as 1 cycle, 250 cycles were repeated.

Process (1): A process of performing deposition at a pressure of 100 Pa for 10 seconds by introducing vapor of the raw material for CVD into the reaction chamber, the vapor being obtained by vaporizing the raw material under the conditions of a raw material container heating temperature of 70° C. and a raw material container pressure of 100 Pa.

Process (2): A process of removing the unreacted raw material by performing Ar purge for 10 seconds.

Process (3): A process of performing reaction at a pressure of 100 Pa for 60 seconds by introducing the reactive gas into the reaction chamber.

Process (4): A process of removing the unreacted raw material by performing Ar purge for 10 seconds.

Film thickness measurement by X-ray reflectivity, and analysis of structure and composition of the thin film by X-ray diffraction and X-ray photoelectron spectroscopy were performed on each of the metallic tantalum thin films obtained by performing processes set forth above. As a result, all of the obtained thin films had a thickness of 2 nm to 7 nm, and all of the thin films had a composition of metallic tantalum. Carbon content in each of the thin films was less than about 5.0 atom %. In addition, the thickness of the film obtained for every 1 cycle of the ALD process ranged from about 0.01 nm to about 0.03 nm.

From the results of Example 6, it may be seen that when the tantalum compound according to an embodiment was used as the raw material for the ALD process, a good-quality metallic tantalum thin film was formed, e.g., due to the low amount of carbon in the film.

By way of summation and review, a raw material compound for forming thin films may be desirable. The raw material may be able to suppress undesired impurities in a tantalum-containing thin film upon formation of the thin film, may be able to provide excellent filling properties and excellent step coverage even in a narrow and deep space having a high aspect ratio, and may have an advantage in terms of process stability and mass productivity due to easy handling of the raw material compound. In some solid-state Ta precursors, e.g. pentakis(dimethylamino)Ta (PDMAT), surface area of the solid Ta source may change with time during a deposition process, thereby causing variation in deposition rate for forming a Ta-containing film and deteriorating mass production efficiency. Further, the solid-state Ta precursor in the form of a powder may generate unwanted particles during delivery. In some liquid-state Ta compounds, e.g. tert-butylimido-tris-ethylmethylamido-tantalum (TBTEMT), a Ta-containing film (such as a TaN film) may not be free of carbon impurities. For example, a Ta precursor should show a property suitable for an atomic layer deposition (ALD) process for forming a Ta-containing film. The liquid-state Ta compound may not be suitable for a process of forming a thin film using ALD. Even if the liquid-state Ta compound may be used in the process of forming the thin film using ALD, the resultant Ta-containing film may contain a lot of impurities.

The embodiments may provide a tantalum compound, which is a liquid at room temperature.

The embodiments may provide a tantalum compound, which may help suppress undesired impurities in a tantalum-containing thin film upon formation of the thin film and may provide excellent thermal stability, process stability, and mass productivity, the tantalum compound being a raw material compound for forming the tantalum-containing thin film.

The embodiments may provide a method of forming a tantalum-containing thin film of good quality by using a tantalum compound, which may help suppress undesired impurities in the tantalum-containing thin film upon formation of the thin film and may provide excellent process stability and mass productivity.

The embodiments may provide a method of fabricating an integrated circuit device capable of providing desired electrical properties by forming a tantalum-containing thin film of good quality by using a tantalum compound, which may help suppress undesired impurities in the tantalum-containing thin film upon formation of the thin film and may provide excellent process stability and mass productivity.

According to an embodiment, the tantalum compound may exhibit a volatility that is sufficient to be used for a deposition process, and handling and transfer of the tantalum compound may be facilitated since the tantalum compound is in a liquid state at room temperature due to the low melting point thereof. In addition, the tantalum compound may help suppress foreign substances such as carbon residues remaining in a thin film intended to be formed by using a chemical vapor deposition (CVD) or atomic layer deposition (ALD) process, and the tantalum compound may be suitably used as a raw material for forming a tantalum-containing thin film of good quality.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A method of fabricating an integrated circuit device, the method comprising:
   forming a lower structure on a substrate; and
   forming a tantalum-containing film on the lower structure by using a tantalum compound represented by the following General Formula (I):

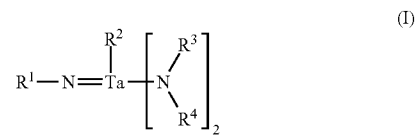

wherein, in General Formula I,
$R^1$, $R^3$, and $R^4$ are each independently a C1 to C10 substituted or unsubstituted linear or branched alkyl, alkenyl, or alkynyl group, or a C4 to C20 substituted or unsubstituted aromatic or alicyclic hydrocarbon group; and
$R^2$ is a hydrogen atom, a C1 to C10 substituted or unsubstituted linear or branched alkyl, alkenyl, or alkynyl group, or a C6 to C20 substituted or unsubstituted aromatic or alicyclic hydrocarbon group.

2. The method as claimed in claim 1, wherein the tantalum compound is a liquid at 25° C. and 1 atm.

3. The method as claimed in claim 1, further comprising forming a capacitor on the substrate such that the capacitor includes a lower electrode, a dielectric film, and an upper electrode,
   wherein:
   forming the lower structure includes forming the lower electrode of the capacitor on the substrate, and
   forming the tantalum-containing film includes forming a tantalum oxide film that covers a surface of the lower electrode.

4. The method as claimed in claim 3, wherein:
   forming the lower electrode includes forming a mold pattern on the substrate such that the mold pattern includes a hole exposing a conductive region of the substrate; and forming the lower electrode such that the lower electrode has a sidewall extending along an inner wall of the hole, and
   forming the tantalum oxide film includes exposing the sidewall of the lower electrode by removing the mold pattern; and forming a $Ta_2O_5$ film that covers the exposed sidewall of the lower electrode.

5. The method as claimed in claim 3, wherein forming the capacitor includes forming a high-K dielectric film that includes a combination of the tantalum-containing film and at least one metal oxide film including a metal that is different from tantalum.

6. The method as claimed in claim 1, wherein:
forming the lower structure includes forming a plurality of fin-shaped active regions that protrude upwardly from the substrate by etching a portion of the substrate; and forming a high-K dielectric film on the plurality of fin-shaped active regions, and
forming the tantalum-containing film includes forming a tantalum nitride film on the high-K dielectric film on the plurality of fin-shaped active regions.

7. The method as claimed in claim 6, wherein forming the tantalum nitride film includes:
forming a tantalum compound-adsorbed layer on the high-K dielectric film by supplying the tantalum compound represented by General Formula (I) onto the high-K dielectric film; and
reacting the tantalum compound-adsorbed layer with a nitrogen atom-containing reactive gas by supplying the reactive gas onto the tantalum compound-adsorbed layer.

8. The method as claimed in claim 6, wherein forming the tantalum nitride film includes supplying the tantalum compound represented by General Formula (I) and a nitrogen atom-containing reactive gas onto the high-K dielectric film.

9. The method as claimed in claim 6, further comprising forming a metal-containing gate layer on the tantalum nitride film on the plurality of fin-shaped active regions, after forming the tantalum nitride film, wherein forming the metal-containing gate layer includes:
forming a first metal-containing film on the tantalum nitride film on the plurality of fin-shaped active regions, the first metal-containing film including a metal that is different from tantalum;
exposing a portion of the tantalum-containing film by etching a portion of the first metal-containing film on a portion of the plurality of fin-shaped active regions and using the tantalum nitride film as an etch stop layer;
cleaning an exposed surface of the tantalum nitride film and an upper surface of the first metal-containing film; and
forming a second metal-containing film that covers the exposed surface of the tantalum nitride film and the upper surface of the first metal-containing film.

10. The method as claimed in claim 9, wherein exposing the portion of the tantalum-containing film by etching the portion of the first metal-containing film includes exposing the portion of the tantalum-containing film by etching the portion of the first metal-containing film with an etch solution that includes $H_2O_2$.

* * * * *